United States Patent [19]
Della Valle et al.

[11] Patent Number: 5,876,744
[45] Date of Patent: Mar. 2, 1999

[54] HIGHLY BIOADHESIVE AND MUCOADHESIVE COMPOSITIONS CONTAINING POLYVINYL ALCOHOL, POLYCARBOPHIL AND BIOPOLYMER FOR THE TREATMENT OF SKIN CONDITIONS AND AS VEHICLES FOR ACTIVE INGREDIENTS

[75] Inventors: Francesco Della Valle; Silvana Lorenzi; Roberto Cerini, all of Padua; Gabriele Marcolongo, Carrara San Giorgio, all of Italy

[73] Assignee: Lifegroup S.p.A., Monselice, Italy

[21] Appl. No.: 776,537

[22] PCT Filed: Jul. 28, 1995

[86] PCT No.: PCT/EP95/02999

§ 371 Date: Apr. 22, 1997

§ 102(e) Date: Apr. 22, 1997

[87] PCT Pub. No.: WO96/03973

PCT Pub. Date: Feb. 15, 1996

[30] Foreign Application Priority Data

Aug. 1, 1994 [IT] Italy ................................. MI94A1668

[51] Int. Cl.⁶ .................................................... A61F 13/00
[52] U.S. Cl. ............................................................ 424/434
[58] Field of Search ............................................... 424/434

[56] References Cited

U.S. PATENT DOCUMENTS

| | | | |
|---|---|---|---|
| 4,615,697 | 10/1986 | Robinson | 604/890 |
| 5,110,605 | 5/1992 | Acharya | 424/487 |

FOREIGN PATENT DOCUMENTS

| | | |
|---|---|---|
| 0 280 807 | 9/1988 | European Pat. Off. . |
| 0 429 156 | 1/1990 | European Pat. Off. . |
| 0 393 904 | 10/1990 | European Pat. Off. . |
| 393904 | 10/1990 | European Pat. Off. . |
| 0 516 026 | 12/1992 | European Pat. Off. . |
| 0 516 141 | 12/1992 | European Pat. Off. . |
| 516026 | 12/1992 | European Pat. Off. . |
| 59-116207 | 10/1984 | Japan . |
| WO 90/10020 | 9/1990 | WIPO . |

OTHER PUBLICATIONS

Barzu et al., *Chemical Abstr.*, vol. 120, #8887, Jan. 3, 1994.
Liberda et al., *Chemical Abstr.*, vol. 127, #5289, 1997.
Sato et al., *Biological Abstr.*, vol. 63, #54687, 1976.
Del Bono et al., *Chemical Abstr.*, vol. 115, #223488, 1991.
Aruffo, Alejandro, et al, "CD44 Is the Principal Cell Surface Receptor for Hyaluronate," *Cell*, vol. 61, Jun. 29, 1990, pp. 1303–1313.
Dol, Frederique, et al, "Pharmacologic properties of a low molecular weight dermatan sulfate: Comparison with unfractionated dermatan sulfate," *J Lab Clin. Med.*, Jan., 1990, pp. 43–51.
Harris, D., et al, GI Transit of Potential Bioadhesive Systems in the Rat, *Journal of Controlled Release*, vol. 12 (1990), pp. 55–65.
Junginger, H. E., "Mucoadhesive Hydrogels," *Pharm. Ind.*, vol. 53, No. 11 (1991), pp. 1056–1065.
Lehr, Claus–Michael, et al, "Effects of the Mucoadhesive Polymer Polycarbophil on the Intestinal Absorption of a Peptide Drug in the Rat," *J. Pharm. Pharmacol.*, vol. 44 (1992), pp. 402–407.
*Martindale The Extra Pharmacopedia*, 23 Ed., Pharmeceutical Press, 1989, p. 1247.
"Polycarbophil Calcium," *Marindale The Extra Pharmacopedia*, 23 Ed., Pharmeceutical Press, 1989, pp. 1103–1104.

(List continued on next page.)

*Primary Examiner*—Thurman K. Page
*Assistant Examiner*—Sharon Howard
*Attorney, Agent, or Firm*—McDermott, Will & Emery

[57] ABSTRACT

Compositions having high bioadhesion, mucoadhesion and visoelasticity, containing mixtures of synthetic polymers, such as polyvinyl alcohol and Polycarbophil, and of biopolymers, such as alginic acid, hyaluronic acid and dermatan sulfate, useful in the treatment of skin and mucosal tissues dryness and dehydration, and suitables as vehicles for active ingredients in percutaneous absorption.

15 Claims, 14 Drawing Sheets

OTHER PUBLICATIONS

Saettone, M.F., et al, "Evaluation of High– and Low–Molecular–Weight Fractions of Sodium Hyaluronate and an Ionic Complex as Adjuvants for Topical Ophthalmic Vehicles Containing Pilocarpine," *International Journal of Pharmaceutics*, vol. 72 (1991), pp. 131–139.

Saettone, M.F., et al, "Evaluation of Muco–Adhesive Properties and in Viro Activity of Ophthalmic Vehicles Based on Hyaluronic Acid," *International Journal of Pharmaceutics*, vol. 51 (1989), pp. 203–212.

Saettone, M.F., et al, "Release of Miconazole From Topical PVA Matrices: Preliminary in Vitro and in Vivo Data," *Journal of Controlled Release*, vol. 16 (1991), pp. 197–202.

Wang, C., et al, "Distribution of Hyaluronan and its CD44 Receptor in the Epithelia of Human Skin Appendages," *Histochemistry*, vol. 98 (1992), pp. 105–112.

Database WPI, Section Ch, Week 8841, Derwent Publications Ltd., London, GB; Class A61, AN 88–289758, "Moisture–retaining lubricating mucosa–protecting agent," & JP, A, 63 212 355 (Katsushima), 5 Sep. 1988.

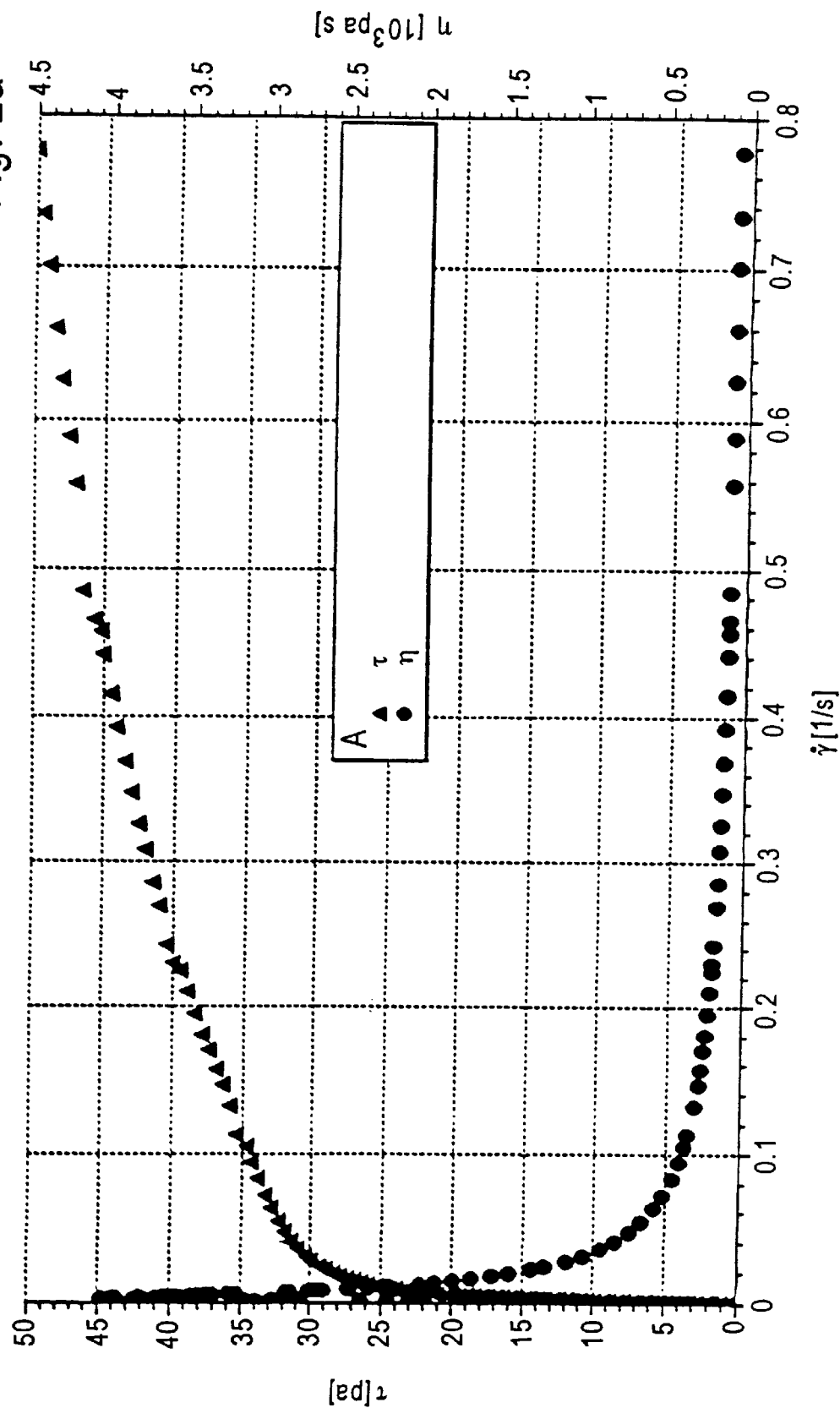

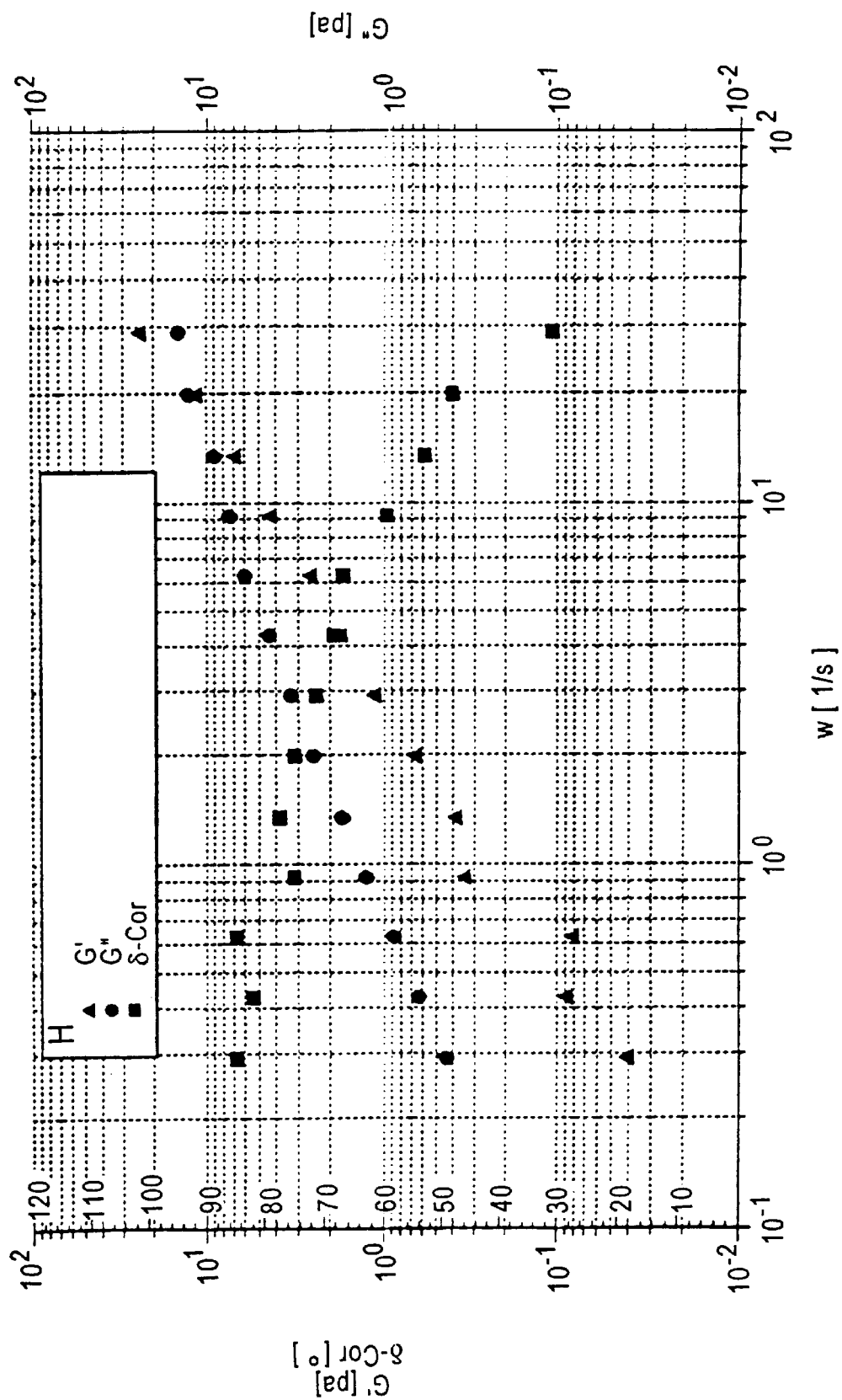

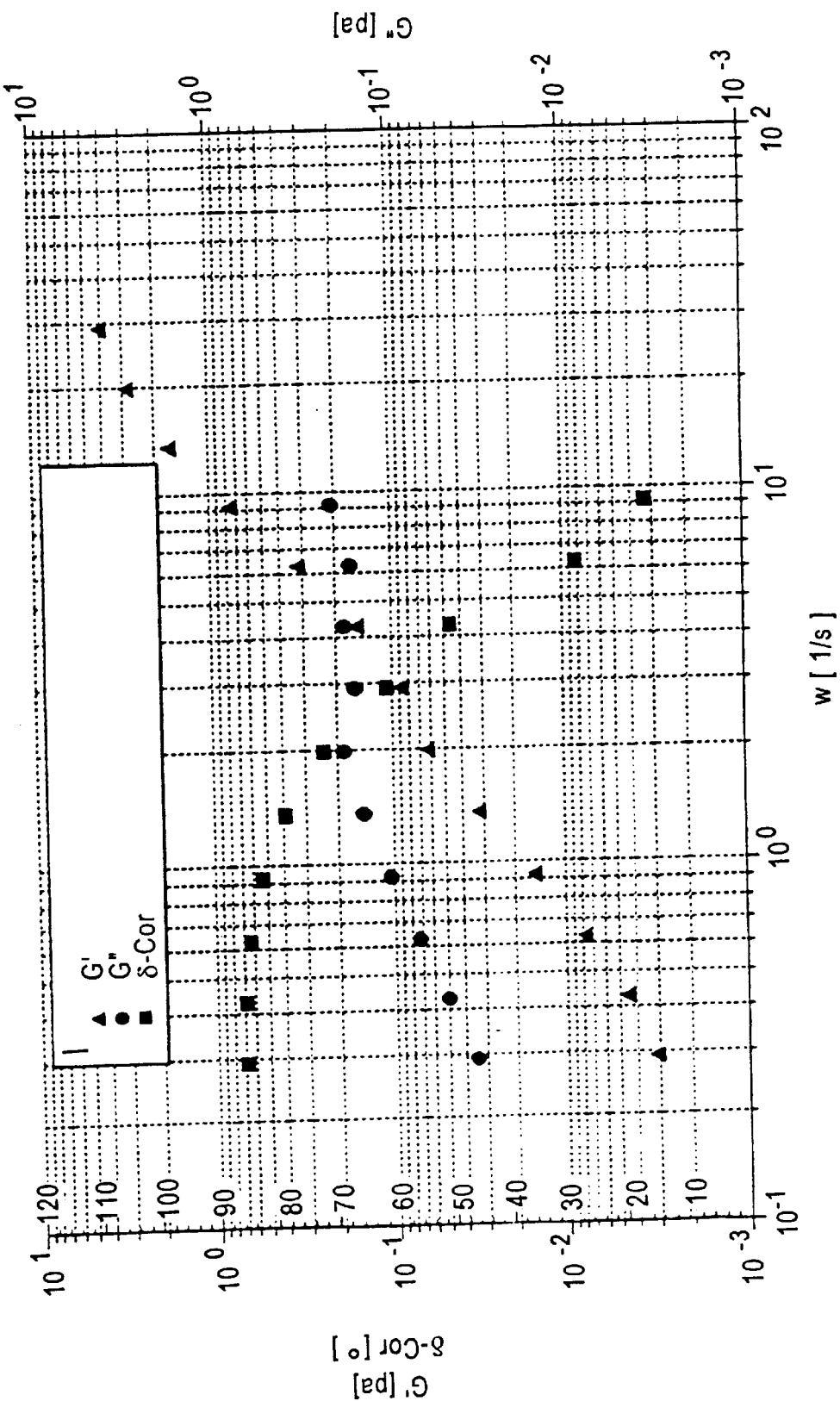

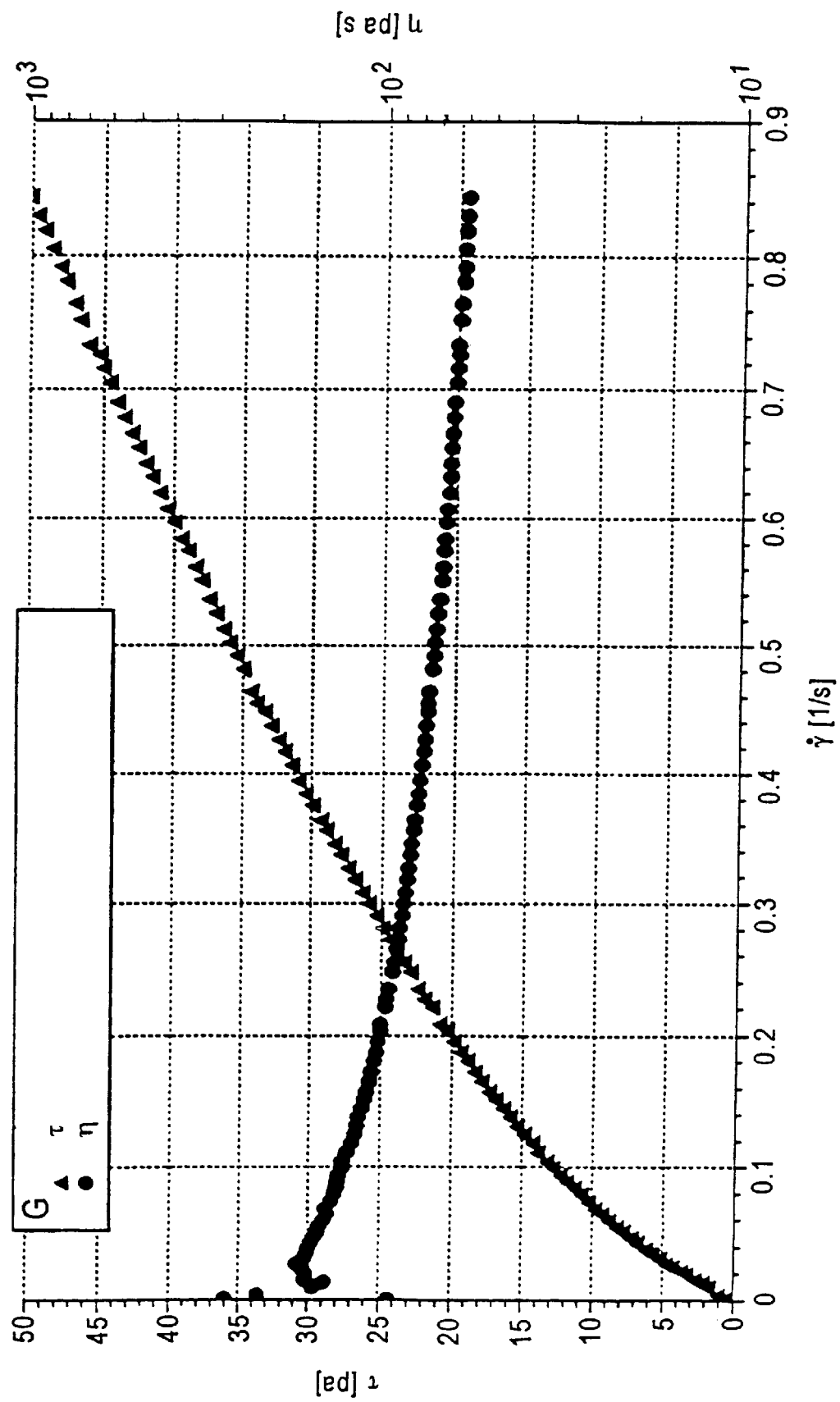

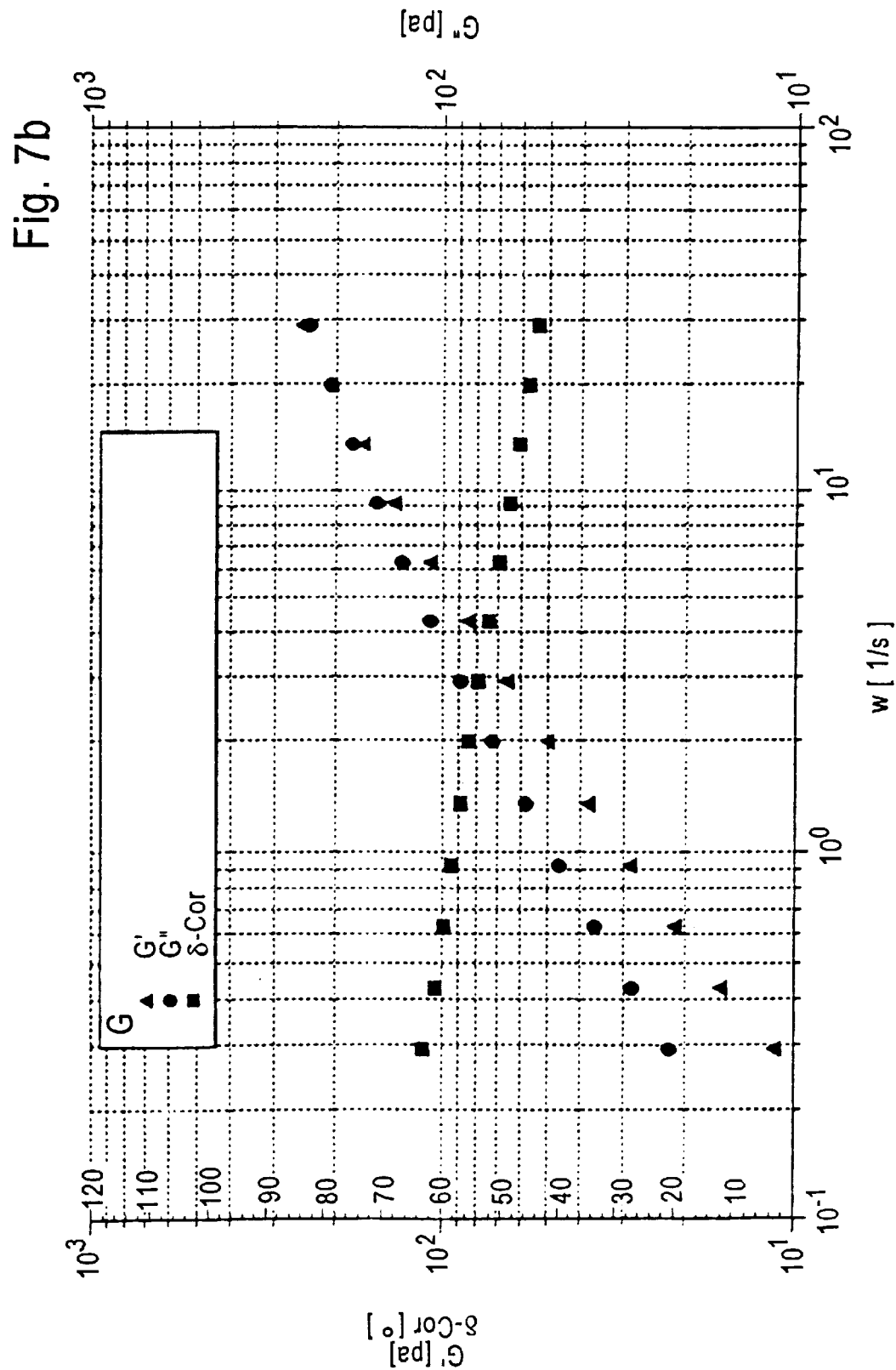

HIGHLY BIOADHESIVE AND MUCOADHESIVE COMPOSITIONS CONTAINING POLYVINYL ALCOHOL, POLYCARBOPHIL AND BIOPOLYMER FOR THE TREATMENT OF SKIN CONDITIONS AND AS VEHICLES FOR ACTIVE INGREDIENTS

FIELD OF THE INVENTION

The present invention relates to aqueous compositions containing mixtures of synthetic polymers and biopolymers, useful in the treatment of skin and mucosal tissues dryness, and suitable as vehicles of active ingredients.

PRIOR ART DISCLOSURE

Skin and mucosal tissues dryness and dehydration are very frequent conditions and may be caused by environmental factors, viruses, bacteria, or associated with etiologically different primary diseases. When affecting mucous membranes, said conditions are usually described as dryness of the buccal cavity (e.g. dry stomatopharyngitis in Sjögren's syndrome), of the vaginal, nasal and intestinal mucous membranes, and dryness of the eye (e.g. keratitis sicca).

Skin dryness and/or dehydration are not only important from an aesthetic point of view, but above all said conditions represent alterations of the cutis physiological function as a protective and defensive barrier. Furthermore, said dryness, which is per se a tissual damage causing lesions in the most serious cases, is also a hindrance to the absorption of possible products and/or drugs that can be administered in the treatment of the diseases affecting said tissues.

The methods most commonly used in the restoration of adequate moisture levels and in the prevention of further dehydration of the tissues consist in the application of creams, lotions or gels, which are capable of supplementing the water content of the tissues with highly hydrophilic agents or capable of forming a hydrophobic impermeable barrier on the tissue to be treated.

In the former case, it is well known in the state of the art the use of small synthetic hydrophilic molecules having humectant properties, such as glycerol, optionally mixed with water; it is also well known the use of macromolecules physiologically present in the tissues such as mucropolysaccharides, i.e. hyaluronic acid, dermatan sulfate and chondroitin sulfate, proteins such as collagen, elastin and placental proteins, having good properties as moisturizers and humectants.

As regards percutaneous absorption of active principles, it is to be stressed that the biological response to an active ingredient is often influenced by factors unrelated to the administered amount of the same principle. In particular, this is typical of topical administrations designed for local effect "in situ" as well as of oral administrations designed for absorption by general routes, which is often incomplete or in any case variable. In fact it is known that the bioavailability of active principles may be limited by the residence and contact times with the surface where absorption has to occur, e.g. the gastrointestinal tract in the case of oral preparations.

Therefore, several research works have lately been oriented to the development of bio- and/or mucoadhesive matrixes capable of binding themselves both to the stratum corneum of the cutis and to the film covering the mucous membranes, in particular the nasal one of the upper respiratory tract, the buccal, rectal, vaginal and ophthalmic ones.

The term "bioadhesion" has traditionally been used to describe the aggregation of biological and non-biological materials, rather than the interaction between materials having both biological origin. When the mucous membrane is covered by mucus, it is necessary to introduce the concept of mucoadhesion, which means that it is the same layer of mucus that comes into close contact with the adhesive substance through a typical "interface" phenomenon involving the interpenetration of the two phases.

Therefore, the "efficiency" of a bioadhesive matrix is influenced by specific physical and thermodynamic parameters, which determine the adhesion strength, and in particular by:

i) the "adhesive" molecular weight (e.g. the polyethylene glycol adhesiveness seems to increase with increasing the molecular weight, up to an optimal value of 4,000,000);

ii) the molecular mobility, which favors diffusion, and a sufficiently high viscosity;

iii) the ability to swell and form gels by osmosis with the substrate;

iv) the presence of functional groups capable of forming hydrogen bonds, such as carboxyl, hydroxyl, amido and sulphate groups.

However, the single parameters, though often related to the bioadhesive properties, are a necessary but not a sufficient condition for an adequate bioadhesive behaviour.

Among the substances having physicochemical properties predisposing to good bioadhesion and/or mucoadhesion, there are the aforesaid polysaccharides of biological derivation from mammalian tissues (hyaluronic acid, dermatan sulfate and chondroitin sulfate) as well as the polysaccharides of vegetable derivation, mostly from algae, such as alginic acid, gellan and other related mucropolysaccharides.

Other polysaccharides and cellulose and derivatives thereof (alkyl and carboxyalkyl), chitosan and chitin.

In addition to such polymers, synthetic polymers belonging to the families of polyethylene glycols, polyvinylpyrrolidone, polyvinyl alcohol and Carbopol are also to be mentioned. An examplary highly hydrophilic and highly bioadhesive polymer is Carbopol Ex-55®, denominated Polycarbophil.

The bioadhesive behaviour of some compounds may be studied by in vitro, in vivo and ex vivo specific methods allowing qualitative and quantitative determinations (H. E. Junginger, *Pharm. Inc.,* 53, 11, 1056–1065, 1991).

Measurements made by said methods showed that Polycarbophil, the polymer mentioned above, has excellent adhesion strength and mucoadhesive properties, which were evaluated to be higher than 200% referred to the properties of pectin, which reference value was assumed 100%, sodium alginate was found to have satisfactory adhesion strength and mucoadhesive properties, evaluated at 126% approx.; instead, the mucoadhesion strength of polyvinyl alcohol was found to be 94.8% (H. E. Junginger, ibid, 1991).

The studies made in order to evaluate the ability of mucoadhesive polymers to act as vehicles of drugs and to release same at a controlled rate showed that some solutions containing Carbopol 934® slow the ileocecal transit (D. Harris et al., *J. of Controlled Release,* 12, 55–56, 1990), while Polycarbophil increases the intestinal absorption of peptidergic drugs (C. M. Lehr et al., *J. Phar. Pharmacol.,* 44, 402–407, 1992), polyvinyl alcohol increases the topical bioavailability of miconazole (M. F. Saettone et al., *J. of Controlled Release,* 16, 197–202, 1991) and sodium hyaluronate significantly increases the bioavailability of pilocarpine (M. F. Saettone, *Int. J. of Pharmaceutics,* 72, 131–139, 1991).

SUMMARY OF THE INVENTION

The Applicant has found aqueous compositions containing mixtures of synthetic polymers and biopolymers at different percent ratios; said mixtures unexceptedly exhibit higher bioadhesive properties than those of the polymers that are now recognized to have said properties to an optimal degree, such as Polycarbophil.

Said mixtures essentially consist of synthetic polymers, such as Polycarbophil and polyvinyl alcohol, associated with biopolymers, such as hyaluronic acid, alginic acid or dermatan sulfate, in the acidic form or in the form of salts thereof, in varying proportions.

The viscous behaviour of said compositions is characterized by particular physicochemical properties that substantially differentiate same from aqueous compositions containing only bioadhesive synthetic polymers; it follows that the topical application of the compositions of the invention is particularly advantageous. Said advantages arise from the bioadhesive and, in particular, the viscoelastic characteristics, as well as from the film-forming properties of said compositions.

It is a further object of the present invention the use of said compositions in the rehydration of skin or mucous membranes and/or as vehicles of active principles by topical application on said tissues.

It is a further object of the present invention to provide new compounds, i.e. dermatan sulfate and hyaluronic acid zinc salts, dermatan sulfate tetrabutylammonium salt, and mixed salts of dermatan sulfate or of hyaluronic acid with biotin and ethylenediamine, or with traumatic acid and ethylenediamine.

BRIEF DESCRIPTION OF THE DRAWINGS

The rheological properties and viscoelastic behaviour of the compositions according to the present invention will be better understood by reference to the enclosed drawings, wherein:

FIGS. 1a to 7a illustrate the flow curves (rheograms) relating respectively to samples B, A, D, H, I, C and G;

FIGS. 1b to 7b illustrate the oscillatory measurements relating respectively to samples B, A, D, H, I, C and G.

DETAILED DESCRIPTION OF THE INVENTION

Figure 1A:
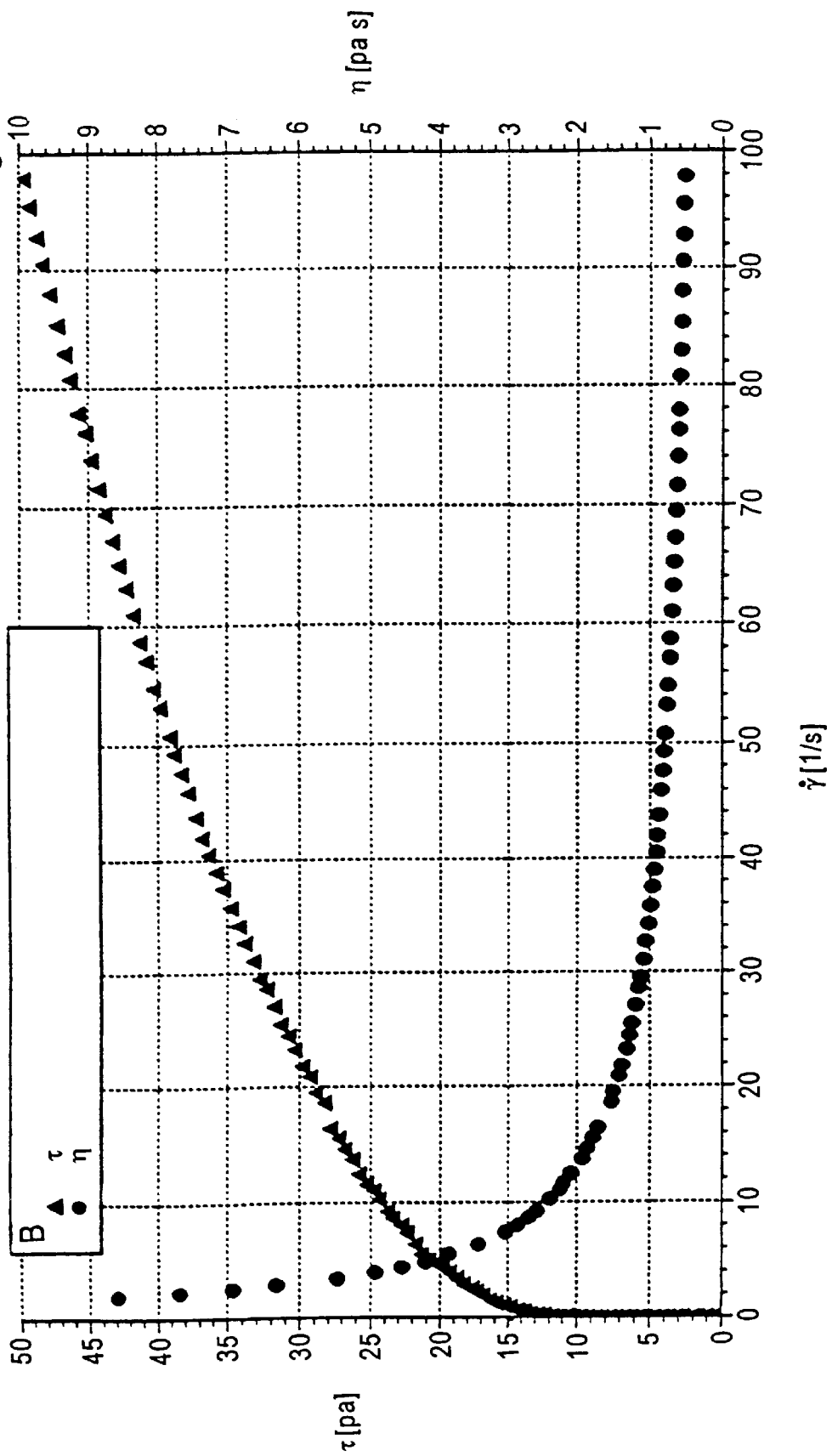

The characteristics and advantages of the compositions according to the present invention will be better illustrated in the following detailed description.

The synthetic polymers used in the compositions of the present invention are selected from the group consisting of polyethylene glycols, polyvinylpyrrolidone, polyvinyl alcohol and derivatives thereof, Carbopol and derivatives thereof; and preferably said synthetic polymers are polyvinyl alcohol or Polycarbophil.

Polyvinyl alcohol is a polymer having formula ($-CH_2-CHOH-$)$_n$, prepared by alcoholysis of polyvinyl acetate.

The polymer found in commerce is characterized by different degrees of acetylation, which determine different physicochemical properties. Depending on the degree of polymerization, it may be soluble in aqueous solutions giving colloidal solutions, or in mixtures of water and alcohol.

This polymer is widely used in the industry of plastics and textiles as a non-ionic surfactant. In the pharmaceutical industry, it is amply used in the ophthalmic field to prepare useful solutions per se, e.g. artifical tears, or as a vehicle of ophthalmic drugs. It is also used in dermatology and for the cosmetic treatment of the skin (Martindale, *Extra Pharmacopeia,* 29th Ed., Pharmaceutical Press, 1989).

The other preferred synthetic polymer is Polycarbophil, a polyacrylic acid cross-linked with divinyl glycol (3,4-dihydroxy-1,5-hexadiene). The main characteristic of this polymer is a high water absorbing power; due to said physicochemical property, it is used in the form of calcium salt as a cathartic (Martindale, *Extra Pharmacopeia,* 29th Ed., Pharmaceutical Press, 1989). The use of said polymer as moisturizer and humectant is disclosed in European patent application No. 0 429 156 A1 and as a bioadhesive vehicle for the controlled release of active principles, in the pharmaceutical field, in U.S. Pat. No. 4,615,697.

The biopolymers used can be obtained from mammalian tissues, such as hyaluronic acid, dermatan sulfate and chondroitin sulfate, which play a key role in differentiation, growth and migration of cells, as well as in extracellular matrix organization; or they can be obtained from vegetables, such as alginic acid. Said polysaccharides are characterized by specific and distinctive functional groups, but they all show a high molecular weight and a marked hydrophilic power.

In particular, alginic acid, a polyuronic acid extracted from algae and composed of mannuronic and L-guluronic acid residues, is amply used in the food industry as thickener and in the pharmaceutical industry as antiacid and, in the form of calcium salt, as haemostatic. Hyaluronic acid and dermatan sulfate, deriving on the opposite from animal tissues, are characterized the former by glucuronic acid and glucosamine, and the latter by iduronic acid and sulphate groups.

Among the above mentioned biopolymers, hyaluronic acid has been particularly studied concerning both its biological role and the pharmacological or cosmetic properties. Recent studies have shown that hyaluronic acid is the most specific ligand of CD44 receptor, a protein localized on cell surface. It is to be noted that CD44 is also able to bind, with a lower affinity, chondroitin-4-sulfate and chondroitin-6-sulfate (Aruffo et al. "CD44 is the principal cell surface receptor for hyaluronate". *Cell,* 61: 1303–1313, 1990). To further specify such a functional interaction, it has been shown that CD44 receptor and hyaluronic acid are co-distributed in epithelia having similar functional program, i.e. keratinizing oral epithelium, hair follicle and nail cells (C. Wang et al. "Distribution of hylauronan and its CD44 receptor in the epithelia of human skin appendages", *Histochemistry,* 98: 105–112, 1992). According to these evidences, hyaluronic acid has found extensive pharmaceutical applications in the osteoarticular, ophthalmic and dermatologic fields and for the cosmetic treatment of the skin. Also its homologue chondroitin sulfate is widely used in the pharmaceutical field as an anti-hyperlipoproteinaemic agent in atherosclerosis and as artifical tears in the form of eyewash.

High molecular weight dermatan sulfate is used because of its anticoagulant properties, analogous to those of heparin. However, said properties are not observed in the low molecular weight polymer (F. Dol et al., *J. Lab. Clin. Med.,* 115, 1, 43–51, 1990).

Moreover, it is noteworthy the fact that the presence in the bioadhesive and mucoadhesive compositions of the invention of biopolymers able to bind, through a well defined epitope, to a specific receptor, such as hyaluronan and CD44, leads to a preferential distribution via receptor-binding of the biopolymers themselves, as well as the active principles optionally delivered.

All the above biopolymers are usually used in the form of sodium salt; however, in the preparation of the aforesaid bioadhesive compositions, they can be used also in the form of other commonly available salts, such as salts of alkali or alkaline-earth metals and ammonic salts.

Furthermore, said biopolymers can be used in the form of new salts, such as lithium and zinc salts, or mixed salts with a diaminic compound, such as ethylenediamine or piperazine, and a biocompatible compound having a carboxylic group, such as biotin or traumatic acid, which form a further object of the present invention. More specifically, salification is carried out by bridging the carboxylic groups of the byopolimer and of said biocompatible compound by means of a suitable organic compound carrying at least two aminic groups, such as for example ethylenediamine or piperazine, or carrying at least two quaternary ammonic substituents. Said mixed salts of biopolymers, according to the present invention, are preferably the salt with biotin and ethylenediamine, and the salt with traumatic acid and ethylenediamine, particularly suitable for supplying oligoelements or vitamins to the tissue (skin or mucous membranes) treated with the compositions of the invention.

The methods for the preparation of the above mentioned salts may vary depending on the polysaccharide nature and physico-chemical characteristics. In fact, some polysaccharides are water-soluble both in the acidic and salified forms (Methods 1 and 2), while some others are poorly water-soluble in the acidic form and soluble in the form of salts (Methods 3 and 4). Finally, other polysaccharides are soluble in the acidic form and water-insoluble in the form of salts (Methods 5 and 6).

We report hereinafter suitable methods of preparation of the aforesaid salts, corresponding to the above cases; some of the them are already known in the state of the art, while others, even if new, are easily deducible by the men skilled in the art.

Said methods allow the obtainment of salts of mono and bivalent ions, as well as of higher-valence ions, which can salify the carboxylic groups of the polysaccharide; moreover, according to the reported preparation procedures, it is possible to obtain salts of the aforesaid biopolymers with primary, secondary or tertiary organic amines, or with quaternary ammonic compounds.

Furthermore, said methods may be conveniently used to obtain the mixed salts of said biopolymers with diaminic compounds and biocompatible compounds having a carboxylic group.

Method I

A quantity of salified polysaccharide in the most currently available form, generally the sodium salt, partially salified to obtain 1.0 equivalent of free anionic functional groups (carboxyls and/or sulphates), is solubilized in distilled water. The solution is eluted in a column cooled to 4° C., containing a slight excess of a cationic exchange resin such as 50×8 Dowex®, generated in H$^+$ form. The sodium-free eluate is collected under continued stirring in a solution cooled to 4° C. and containing an equivalent amount of the counterion with which the polysaccharide is to be salified, properly prepared in the free base form. The obtained product may be collected by precipitation in a non-solvent or by drying processes operating under mild conditions, such as lyophilization or spray-drying.

Method II

A quantity of salified polysaccharide in the most currently available form, generally the sodium salt, partially salified to obtain 1.0 equivalent of free anionic functional groups (carboxyls and/or sulphates), is solubilized in distilled water. The solution is dialyzed at 4° C. vs. an aqueous solution of a salt (MX) of the cation with which the polymer is to be salified until the dialyzate is sodium-free and then vs. distilled water to remove excess MX, if any. The obtained product may be collected by precipitation in a non-solvent or by drying processes operating under mild conditions, such as lyophilization or spray-drying.

Method III

A quantity of salified polysaccharide in the most currently available form, generally the sodium salt, partially salified to obtain 1.0 equivalent of free anionic functional groups (carboxyls and/or sulphates), is solubilized in distilled water. The solution is eluted in a column cooled to 4° C., containing a slight excess of a cationic exchange resin such as 50×8 Dowex®, generated in the ionic form of the counterion with which polymer is to be salified. The product contained in the eluate may be collected by precipitation in a non-solvent or by drying processes operating under mild conditions, such as lyophilization or spray-drying.

Method IV

A quantity of salified polysaccharide in the most currently available form, generally the sodium salt, partially salified to obtain 1.0 equivalent of free anionic functional groups (carboxyls and/or sulphates), is solubilized in distilled water. The solution is slowly added with an equivalent amount of mineral acid, under continued stirring, at 4° C. The polysaccharide that precipitates in the acidic form is separated by filtration, washed and suspended again in distilled water at 4° C. An equivalent amount of the counterion with which the polymer is to be salified, properly prepared in the free base form is added to the polymer suspension in the acidic form. The soluble salt obtained by salification may be collected by precipitation in a non-solvent or by drying processes operating under mild conditions, such as lyophilization or spray-drying.

Method V

A quantity of polysaccharide partially salified with an alkaline earth metal (Ca$^{++}$ or Ba$^{++}$) to obtain 1.0 equivalent of free anionic functional groups (carboxyls and/or sulphates), is solubilized in distilled water. The solution is added slowly and under continued stirring with an equivalent amount of a suitable salt of the counterion with which the polymer is to be salified, properly salified with an anion bringing about the formation of a precipitate with the alkaline earth metal; the formation of insoluble calcium or barium sulphate will be particularly convenient. The precipitate is separated by filtration and discarded, while the product contained in the solution may be collected by precipitation in a non-solvent or by drying processes operating under mild conditions, such as lyophilization or spray-drying.

Method VI

A quantity of salified polysaccharide in the most currently available soluble form, generally the sodium salt, partially salified to obtain 1.0 equivalent of free anionic functional groups (carboxyls and/or sulphates), is solubilized in distilled water. The solution is added slowly and under continued stirring with an equivalent solution of a convenient salt of the cation with which the polymer is to be salified, preferably a halide, sulphate, nitrate or acetate of said cation. The precipitate is separated by filtration, washed and dried under vacuum, while the solution is discarded.

We report hereinbelow for illustrative but not limitative purposes the following examples describing the preparation of the new hyaluronic acid and dermatan sulfate salts of the present invention, according to the general methods described above.

EXAMPLE 1
Preparation of dermatan sulfate lithium salt

Dermatan sulfate sodium salt (25.2 g), having an average molecular weight of 5,000 to 8,000 daltons, was solubilized in distilled water (200 ml). The solution was eluted in a column cooled to 4° C., containing the cationic exchange resin 50×8 Dowex® (120 ml), generated in $Li^+$ form. The sodium-free eluate was frozen and lyophilized to give 23.3 g of product.

The physicochemical properties of the dermatan sulfate lithium salt are as follows:

| | |
|---|---|
| physical state | whitish amorphous powder |
| empirical formula | $C_{14}H_{19}NO_{14}SLi_2$ |
| molecular weight | 471.26 (disaccharide unit) |
| elemental analysis | |
| theoretical: | C = 35.68%; H = 4.06%; N = 2.97%; |
| | O = 47.53%; S = 6.80%; |
| | Li = 2.95% |
| experimental: | C = 35.55%; H = 4.10%; N = 2.92%; |
| | O = 47.70%; S = 6.68%; |
| | Li = 2.90% |
| water solubility | >10 mg/ml |

EXAMPLE 2
Preparation of dermatan sulfate zinc salt

Dermatan sulfate sodium salt (25.2 g), having an average molecular weight of 5,000 to 8,000 daltons, was solubilized in distilled water (200 ml). The solution was eluted in a column cooled to 4° C., containing the cationic exchange resin 50×8 Dowex® (120 ml), generated in $Zn^{++}$ form. The sodium-free eluate was frozen and lyophilized to give 26.05 g of product.

The physicochemical properties of the dermatan sulfate zinc salt are as follows:

| | |
|---|---|
| physical state | whitish amorphous powder |
| empirical formula | $C_{14}H_{19}NO_{14}SZn$ |
| molecular weight | 522.74 (disaccharide unit) |
| elemental analysis | |
| theoretical: | C = 32.17%; H = 3.66%; N = 2.68%; |
| | O = 42.85%; S = 6.13%; |
| | Zn = 12.51% |
| experimental: | C = 32.05%; H = 3.72%; N = 2.63%; |
| | O = 42.92%; S = 6.15%; |
| | Zn = 12.48% |
| water solubility | >10 mg/ml |

EXAMPLE 3
Preparation of hyaluronic acid zinc salt

Hyaluronic acid sodium salt (40.1 g), having an average molecular weight of 1,000,000 daltons, was solubilized in distilled water (8,000 ml). The solution was eluted in a column cooled to 4° C., containing the cationic exchange resin 50×8 Dowex® (120 ml), generated in $Zn^{++}$ form. The sodium-free eluate was frozen and lyophilized to give 40.8 g of product.

The physicochemical properties of the hyaluronic acid zinc salt are as follows:

| | |
|---|---|
| physical state | whitish amorphous powder |
| empirical formula | $C_{14}H_{20}N_{11}Zn_{1/2}$ |
| molecular weight | 411.0 (disaccharide unit) |
| elemental analysis | |
| theoretical: | C = 40.91%; H = 4.90%; N = 3.41%; |
| | O = 42.82%; Zn = 7.95% |
| experimental: | C = 40.80%; H = 4.97%; N = 3.38%; |
| | O = 43.00%; Zn = 7.81% |
| water solubility | >5 mg/ml |

EXAMPLE 4
Preparation of dermatan sulfate mixed salt with biotin and ethylenediamine Dermatan sulfate sodium salt (50.3 g), having an average molecular weight of 5,000 to 8,000 daltons, was solubilized in distilled water (500 ml). The solution was eluted in a column cooled to 4° C., containing the cationic exchange resin 50×8 Dowex® (240 ml), generated in $H^+$ form. The sodium-free eluate was collected under continued stirring in a solution cooled to 4° C., containing biotin (48.8 g) and ethylenediamine (12.0 g). The resulting solution was frozen and lyophilized to give 106.2 g of product.

The physicochemical properties of the low molecular weight dermatan sulfate mixed salt with biotin and ethylenediamine are as follows:

| | |
|---|---|
| physical state | whitish amorphous powder |
| empirical formula | $C_{38}H_{69}N_9O_{20}S_3$ |
| molecular weight | 1068.19 (disaccharide unit) |
| elemental analysis | |
| theoretical: | C = 42.73%; H = 6.51%; N = 11.80%; |
| | O = 29.96%; S = 9.00% |
| experimental: | C = 42.65%; H = 6.60%; N = 11.64%; |
| | O = 29.74%; S = 6.25% |
| biotin | 45.74% (w/w) |
| water solubility | >10 mg/ml |

EXAMPLE 5
Preparation of dermatan sulfate mixed salt with traumatic acid and ethylenediamine Dermatan sulfate sodium salt (50.3 g), having an average molecular weight of 5,000 to 8,000 daltons, was solubilized in distilled water (500 ml). The solution was eluted in a column cooled to 4° C., containing the cationic exchange resin 50×8 Dowex® (240 ml), generated in $H^+$ form. The sodium-free eluate was collected under continued stirring in a solution cooled to 4° C., containing traumatic acid (22.8 g) and ethylenediamine (12.0 g). The resulting solution was frozen and lyophilized to give 80.3 g of product.

The physicochemical properties of the low molecular weight dermatan sulfate mixed salt with traumatic acid and ethylenediamine are as follows:

| | |
|---|---|
| physical state | whitish amorphous powder |
| empirical formula | $C_{30}H_{57}N_5O_{18}S$ |
| molecular weight | 807.86 (disaccharide unit) |
| elemental analysis | |
| theoretical | C = 44.60%; H = 7.11%; N = 8.67%; |
| | O = 35.65%; S = 3.97% |
| experimental: | C = 44.65%; H = 7.18%; N = 8.54%; |
| | O = 35.72%; S = 3.91 |
| traumatic acid | 28.26% (w/w) |
| water solubility | >10 mg/ml |

EXAMPLE 6
Preparation of hyaluronic acid mixed salt with biotin and ethylenediamine Hyaluronic acid sodium salt (40.1 g), having an average molecular weight of 1,000,000 daltons, was solubilized in distilled water (8,000 ml). The solution was eluted in a column cooled to 4° C., containing the cationic exchange resin 50×8 Dowex® (120 ml), generated in $H^+$ form. The sodium-free eluate was collected under continued stirring in a solution cooled to 4° C., containing biotin (24.4 g) and ethylenediamine (6.0 g). The resulting solution was frozen and lyophilized to give 67.9 g of product.

The physicochemical properties of the high molecular weight hyaluronic acid mixed salt with biotin and ethylenediamine are as follows:

| physical state | whitish amorphous powder |
|---|---|
| empirical formula | $C_{26}H_{45}N_5O_{14}S$ |
| molecular weight | 683.73 (disaccharide unit) |
| elemental analysis | |
| theoretical: | C = 45.67%; H = 6.63%; N = 10.24%; O = 32.67%; S = 4.69% |
| experimental: | C = 45.24%; H = 6.85%; N = 10.18%; O = 33.12%; S = 4.61% |
| biotin | 35.73% (w/w) |
| water solubility | >10 mg/ml |

EXAMPLE 7

Preparation of hyaluronic acid mixed salt with traumatic acid and ethylenediamine Hyaluronic acid sodium salt (40.1 g), having an average molecular weight of 1,000,000 daltons, was solubilized in distilled water (8,000 ml). The solution was eluted in a column cooled to 4° C., containing the cationic exchange resin 50×8 Dowex® (120 ml), generated in $H^+$ form. The sodium-free eluate was collected under continued stirring in a solution cooled to 4° C., containing traumatic acid (11.4 g) and ethylenediamine (6.0 g). The resulting solution was frozen and lyophilized to give 67.9 g of product.

The physicochemical properties of the high molecular weight hyaluronic acid mixed salt with traumatic acid and ethylenediamine are as follows:

| physical state | whitish amorphous powder |
|---|---|
| empirical formula | $C_{22}H_{39}N_3O_{13}$ |
| molecular weight | 553.56 (disaccharide unit) |
| elemental analysis | |
| theoretical: | C = 47.74%; H = 7.10%; N = 7.59%; O = 37.57% |
| experimental: | C = 47.34%; H = 7.18%; N = 7.46%; O = 38.02% |
| traumatic acid | 20.62% (w/w) |
| water solubility | >10 mg/ml |

EXAMPLE 8

Preparation of dermatan sulfate tetrabutylammonium salt

Dermatan sulfate sodium salt (25.2 g), having an average molecular weight of 5,000 to 8,000 daltons, was solubilized in distilled water (200 ml). The solution was eluted in a column cooled to 4° C., containing the cationic exchange resin 50×8 Dowex® (120 ml), generated in the tetrabutylammonium form. The sodium-free eluate was frozen and lyophilized to give 47.0 g of product.

The physicochemical properties of the dermatan sulfate tetrabutylammonium salt are as follows:

| physical state | whitish amorphous powder |
|---|---|
| empirical formula | $C_{46}H_{93}N_3O_{14}S$ |
| molecular weight | 944.33 (disaccharide unit) |
| elemental analysis | |
| theoretical: | C = 58.51%; H = 9.93%; N = 4.45%; O = 23.72%; S = 3.40% |
| experimental: | C = 58.23%; N = 10.01%; N = 4.51%; O = 23.78%; S = 3.47% |
| water solubility | >10 mg/ml |

The bioadhesive and mucoadhesive compositions according to the present invention contain synthetic and biological polymers preferably at the following concentrations: polyvinyl alcohol, at a concentration ranging from 0.1 to 4% by wt., Polycarbophil at a concentration ranging from 0.1 to 2% by wt., hyaluronic acid having an average molecular weight of 800,000 to 1,200,000 daltons or salts thereof at a concentration ranging from 0.05% to 5% by wt., low and medium viscosity alginic acid or salts thereof at a concentration ranging from 0.5% to 5% by wt., dermatan sulfate having average molecular weight of 5,000 to 8,000 daltons and salts thereof at a concentration ranging from 0.05% to 5% by wt.

The bioadhesive and viscoelastic aqueous compositions of the invention may consist of binary, ternary or quaternary associations of said synthetic and biological polymers, depending on the requirements as well as on the desired degree of bioadhesion and/or physicochemical and rheological properties.

Due to their physicochemical properties, such bioadhesive compositions adhere to mammalian skin and mucous membranes, moisturizing and protecting same from irritative agents. Furthermore, they may usefully be employed in the administration of active principles: in fact, compared with non-bioadhesive matrixes, they improve bioavailability of active principles by prolonging the contact time with the skin or mucosa. In fact, bio- and mucoadhesive bases are active "in loco" for approx. 10–20 hours, i.e. for the period equivalent to the time of turnover of the strata cornea of the epidermis or of mucin. Therefore, a prolonged contact time results in an improved absorption of the active principle.

Furthermore, compared with the compositions known in the state of the art, the claimed compositions, which contain both biopolymers and synthetic polymers, offer the advantage of a higher biocompatibility with the contacted tissues, when applied to the site where they have to exert their action.

Therefore, the bioadhesive compositions according to the present invention are suitable for the prevention and treatment of conditions characterized by excessive skin and mucous membranes dryness (of the mouth, nose, upper respiratory tract, gastrointestinal tract, eye and vagina), even when induced by irritants and physiopathologic causes. Furthermore, being primarily capable of correcting the skin and mucous membranes alterations caused by dehydration, the bioadhesive compositions of the invention also act as vehicles of active principles, whereby the active principles bioavailability is improved, the residence time "in situ" prolonged and/or the absorption improved.

The bioadhesive compositions according to the present invention are prepared by a method consisting of sequential steps. It is described herein by way of example, for illustrative but not limitative purposes, the preparation of a composition containing two synthetic polymers (Polycarbophil and polyvinyl alcohol), a biopolymer (hyaluronic acid) and triethanolamine as salifying agent of the polymers and as thickener.

EXAMPLE 9
Preparation of the compositions of the invention

1) A planetary turboemulsifier of stainless steel provided with paddles counterrotating at variable speed and with heating/cooling jacket was fed, under constant agitation, in the order with demineralized water (50% by wt. of the total) and Polycarbophil. The turboemulsifier was worked under vacuum at −76 mmHg, for at least 15 min.

Once turboemulsifying had been completed, the mass was maintained under stirring at high shear rates until perfect homogenization.

2) At the same time, a melter of stainless steel, equipped with heating jacket and counterrotating paddles, was fed in the order with demineralized water (35.55% by wt. of the total) and polyvinyl alcohol. The melter was heated to 85±2° C. At that temperature, the mass was maintained under mixing until a perfectly clear solution was obtained.

3) Once the two aforesaid steps had been completed, the mass contained in the melter was added slowly, under continuous stirring and in a thin stream, to the mass contained in the planetary turboemulsifier, whose inside was maintained under constant vacuum. The resulting mass was maintained under continuous stirring until a completely homogeneous phase was obtained. The resulting mass was cooled under vacuum to 30±2° C. At that temperature, the mass was maintained under stirring and in vacuo.

4) Solution A was separately prepared in a suitable vessel of stainless steel, provided with agitator, by addition in the order of demineralized water (10% by wt. of total) and of a biopolymer, e.g. hyaluronic acid. Agitation was continued until a viscous, perfectly homogoneous and clear solution was obtained.

5) Solution A was added slowly and in a thin stream to the mass contained in the turboemulsifier, under continuous stirring and under constant vacuum at −76 mmHg. Agitation was continued until a perfectly homogeneous mass was obtained.

A gel of the desired density may be obtained by adding for example triethanolamine and operating according to the following steps, subsequent to step 5);

6) Solution B consisting of demineralized water (1% by wt. of the total) and triethanolamine was prepared instantly in a suitable vessel of stainless steel.

7) Solution B was added under continuous stirring to the mass contained in the turboemulsifier. Agitation was continued until complete carbomers swelling and a perfectly homogeneous gel were obtained. Once the mass had gelled completely, mixing was stopped and the pressure inside the turboemulsifier was slowly restored. The gelled mass was then discharged into containers of stainless steel.

For illustrative but not limitative purposes, the physicochemical properties of the compositions according to the present invention, obtained by the aforesaid method, are herein reported in Table 1. Concentrations are by weight: balance to 100 is water.

TABLE 1

Physiochemical properties of bioadhesive formulations

| Bioadhesive comp. | Conc. % | pH | Viscosity | Density | Ref. |
|---|---|---|---|---|---|
| Polycarbophil | 1.00 | 5.2 ± 0.5 | 3,100 | 1.0050 | C |
| Polyvinyl alcohol | 1.50 | | | | |
| Hyaluronic acid | 0.15 | | | | |
| Polycarbophil | 0.20 | 5.3 ± 0.5 | 230 | 1.0020 | D |
| Polyvinyl alcohol | 0.30 | | | | |
| Hyaluronic acid | 0.15 | | | | |

TABLE 1-continued

Physiochemical properties of bioadhesive formulations

| Bioadhesive comp. | Conc. % | pH | Viscosity | Density | Ref. |
|---|---|---|---|---|---|
| Polycarbophil | 1.00 | 6.8 ± 0.5 | 2,700 | 1.0100 | E |
| Polyvinyl alcohol | 1.50 | | | | |
| Sodium Alginate | 1.00 | | | | |
| Polycarbophil | 1.00 | 6.5 ± 0.5 | 6,000 | 1.0200 | F |
| Polyvinyl alcohol | 1.50 | | | | |
| Sodium Alginate | 2.00 | | | | |
| Polycarbophil | 1.00 | 6.6 ± 0.5 | 10,000 | 1.0250 | G |
| Polyvinyl alcohol | 1.50 | | | | |
| Sodium Alginate | 3.00 | | | | |
| Polycarbophil | 0.20 | 5.2 ± 0.5 | 400 | 1.0050 | H |
| Polyvinyl alcohol | 1.50 | | | | |
| Hyaluronic acid | 0.30 | | | | |
| Polycarbophil | 0.20 | 5.2 ± 0.5 | 50 | 1.0050 | I |
| Polyvinyl alcohol | 1.50 | | | | |
| Dermatan sulfate | 0.15 | | | | |

Viscosity, expressed as centipoises (cp) at 20° C., was measured with a viscometer CONTRAVES ® TVB.
Density (relative 20/20° C.) was measured with a picnometer for semifluids vs. the density of water.

Measurement of bioadhesive properties

In order to check the bioadhesive properties, the adhesion strength of the aforesaid compositions (marked C to I) was evaluated in comparison with mucin, Carbopol 940® and the bioadhesive polymer Polycarbophil at a concentration of 1% by wt. (composition A) and of 0.20% by wt. (composition B) in water, i.e. at the concentrations at which said polymer exhibited the best mucoadhesive properties (Junginger, op. cit., 1991).

In particular, the adhesion work, i.e. the force of adhesion (separation) by elongation of the mucin surfaces, was measured. The tests were carried out according to the methods described in literature (Saettone et al., Int.J.Pharm., 51, 203–212, 1989), in the absence of dipping solution.

The formulation under examination (75 $\mu$l) was stratified on the upper support provided with a centrally pierced ring nut limiting the surface (inside diameter of 1.20 cm). The measurement (platform fall rate 2.50 mm/min) was made after 1 min of contact between the surfaces.

The data obtained by recording the force (F) required for separating the two surfaces (formulation and mucous layer), as a function of the elongation (l) of same, were processed by a computer. The area under the curve obtained (AUC), representing the adhesion work (L) (F,l), was thus calculated.

Table 2 shows the values and the average values ±S.E. (expressed as erg/cm2) of the AUCs of the compositions under investigation as well as the average values of a reference formulation (polyacrylic acid [Carbopol 940®]. 2.5% neutralized gel) and of mucin (swine gastric mucin [Tokyo Kasei Kogyo, Japan], 25.0% dispersion).

TABLE 2

AUC values of bioadhesive matrices.

| comp. n* | A | B | C | D | E | F | G | H | I | C940® | Mucin |
|---|---|---|---|---|---|---|---|---|---|---|---|
| 1 | 457.08 | 381.11 | 608.13 | 398.91 | 497.01 | 803.46 | 742.69 | 474.00 | 524.36 | | |
| 2 | 361.15 | 339.88 | 601.62 | 485.29 | 637.65 | 666.30 | 861.40 | 554.74 | 483.99 | | |
| 3 | 375.47 | 438.41 | 539.98 | 499.18 | 760.06 | 579.92 | 923.26 | 619.85 | 402.82 | | |
| 4 | 374.60 | 411.06 | 462.72 | 408.89 | 539.98 | 576.44 | 793.04 | 520.45 | 489.19 | | |
| 5 | 441.45 | | 460.11 | 405.85 | 553.00 | | 993.58 | 428.86 | 380.68 | | |
| 6 | | | | | | | 827.55 | 574.27 | | | |
| average | 401.95 | 392.61 | 534.51 | 439.62 | 597.54 | 656.53 | 856.92 | 528.69 | 456.21 | 304.23 | 118.20 |
| S.E. | 19.64 | 21.12 | 32.13 | 21.65 | 46.60 | 53.20 | 37.00 | 28.34 | 27.44 | 26.63 | 9.00 |

The experimental results prove that Polycarbophil has excellent bioadhesiveness and adhesion strength and that there is no significant difference between the bioadhesive properties of Polycarbophil at a concentration of 1% by wt. (A) and at a concentration of 0.2% by wt. (B). The mucoadhesion strength of all tested formulations (C to I) is much higher than that of mucin and of C940®, and even of Polycarbophil (A and B), which suggests that the association of biopolymers at different concentrations can improve the adhesion strength and therefore mucoadhesive properties.

Measurements of rheological properties

In order to check whether said compositions, besides exhibiting improved bioadhesive properties, also had significant rheological properties, viscosity measurements, flow curves and oscillatory measurements were carried out to evaluate the viscoelastic behaviour.

Viscosity measurements and flow curves

The samples (A,B,C,D,G,H, and I) were analyzed with a viscometer HAAKE® RS100, with flat-cone measurement systems C35/4° at 23° C., and compared within the same range of applied stress (0–50 Pa). Flow curves (rheograms) were recorded (FIGS. 1a to 7a): the conical rotor was subjected to a shear rate and, at the same time, stress $\tau$ and viscosity $\eta$ were recorded. Table 3 shows the viscosity values obtained at a constant shear rate $\dot{\gamma}$. A shear rate of 50 $sec^{-1}$ was chosen for low viscosity samples and a shear rate of 0.5 $sec^{-1}$ for high viscosity samples.

Figure 1B:
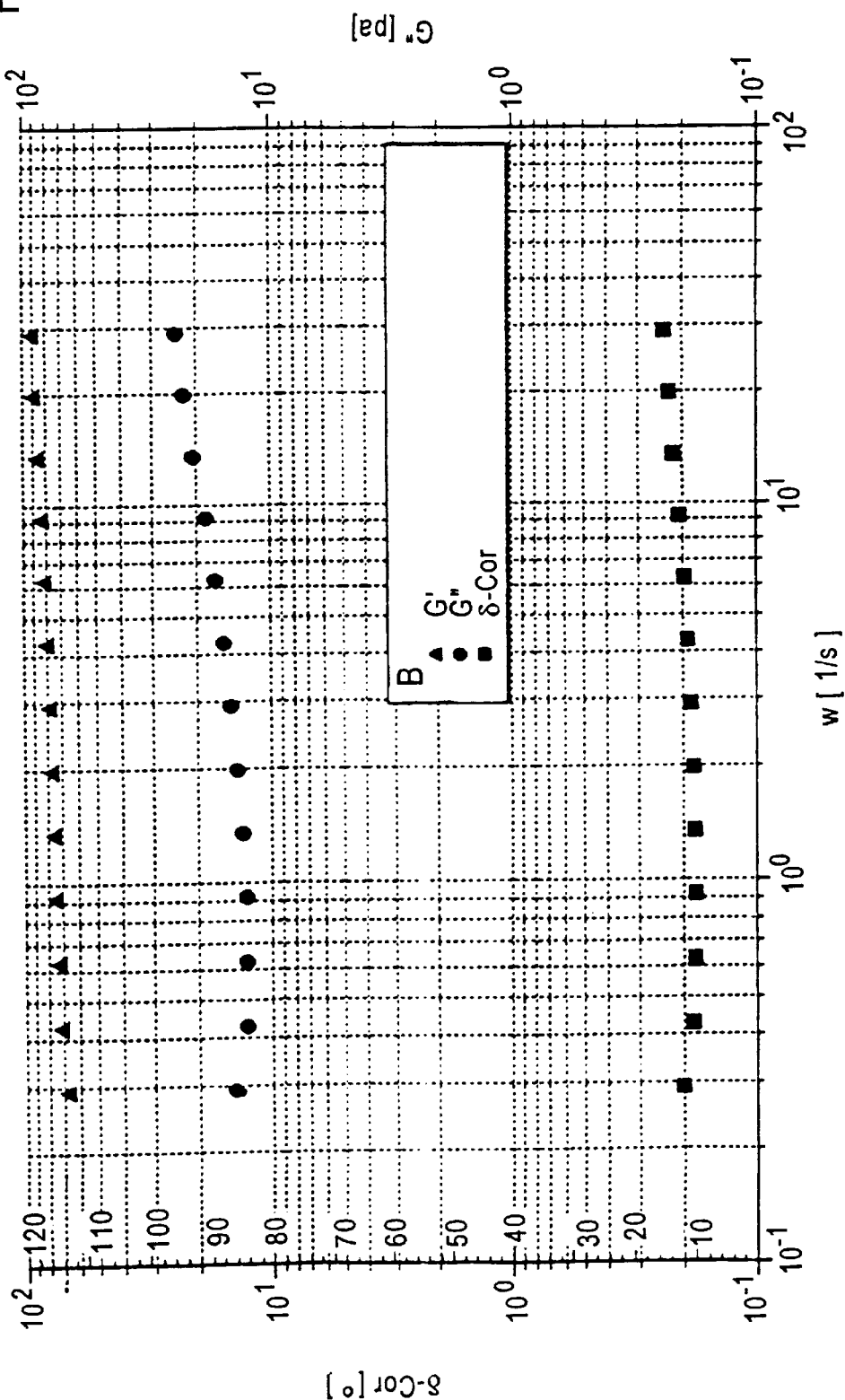

Sample B (0.2% Polycarbophil) was found to be a "stiff gel", the elastic modulus (G')/viscous modulus (G") ratio being high. The values of said elastic modulus (G') and viscous modulus (G") are constant and parallel with varying rotor angular speed, which further indicates a "stiff gel" structure. A probable creep limit is observed (FIG. 1b).

Figure 2B:
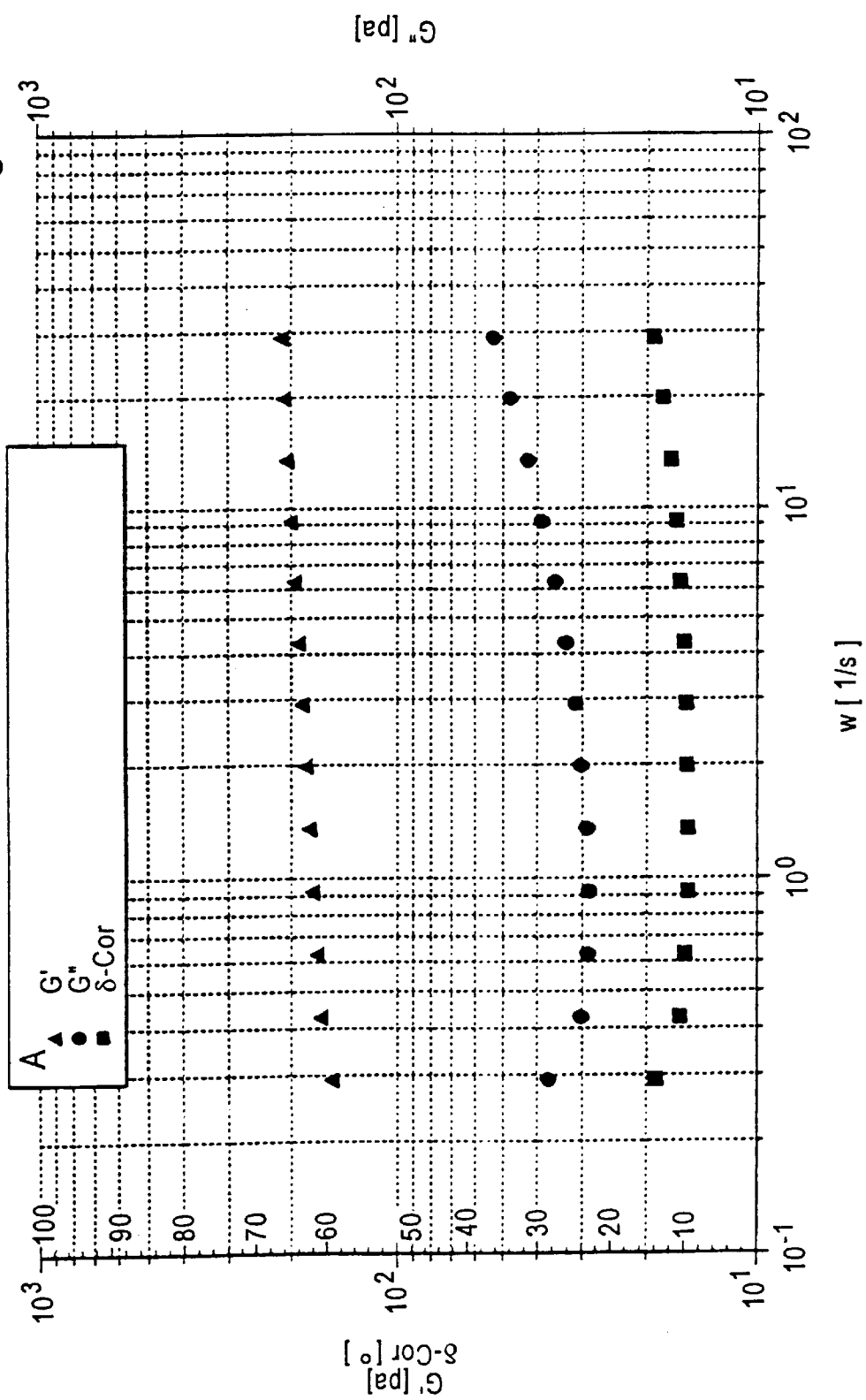

Sample A (1% Polycarbophil) shows an analogous behaviour, but the non-linear, i.e. slightly curvilinear, trend of the δ-Cor angle (displacement angle between vectors G' and G") with varying rotor angular speed indicates a lower stability of the gel, while probable fracture effects appear in its structure (FIG. 2b).

Figure 3A:
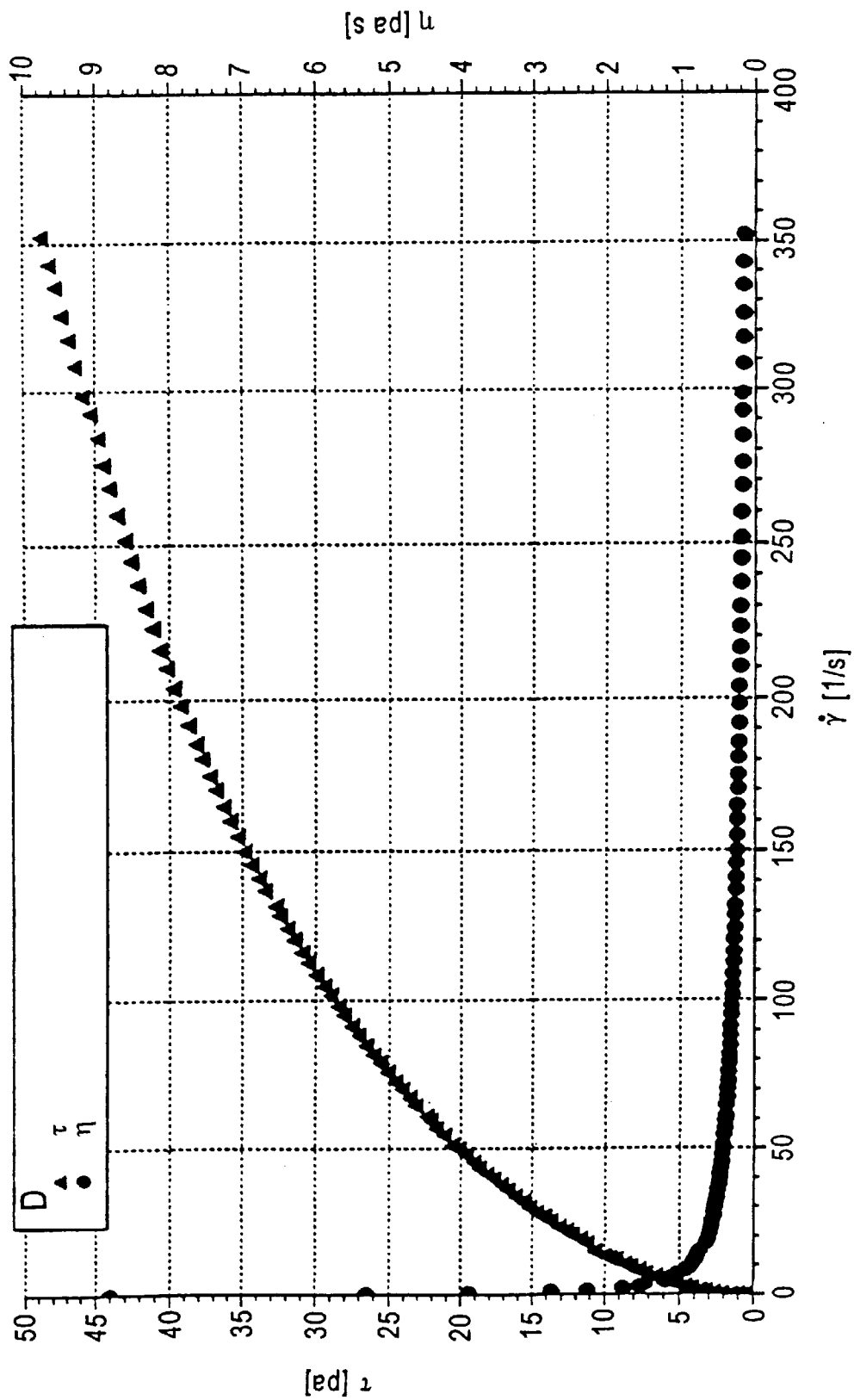
Figure 3B:
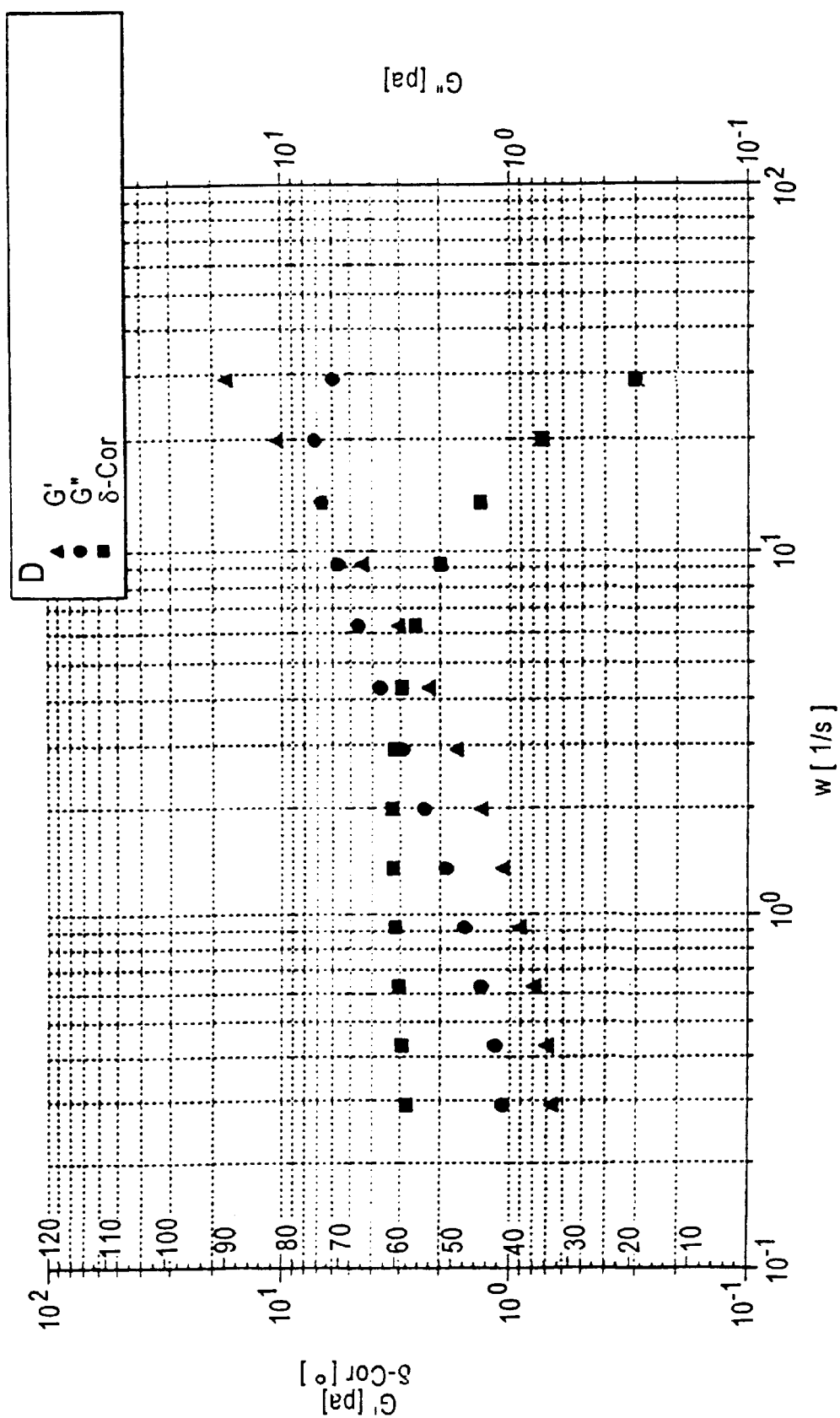
Figure 4A:
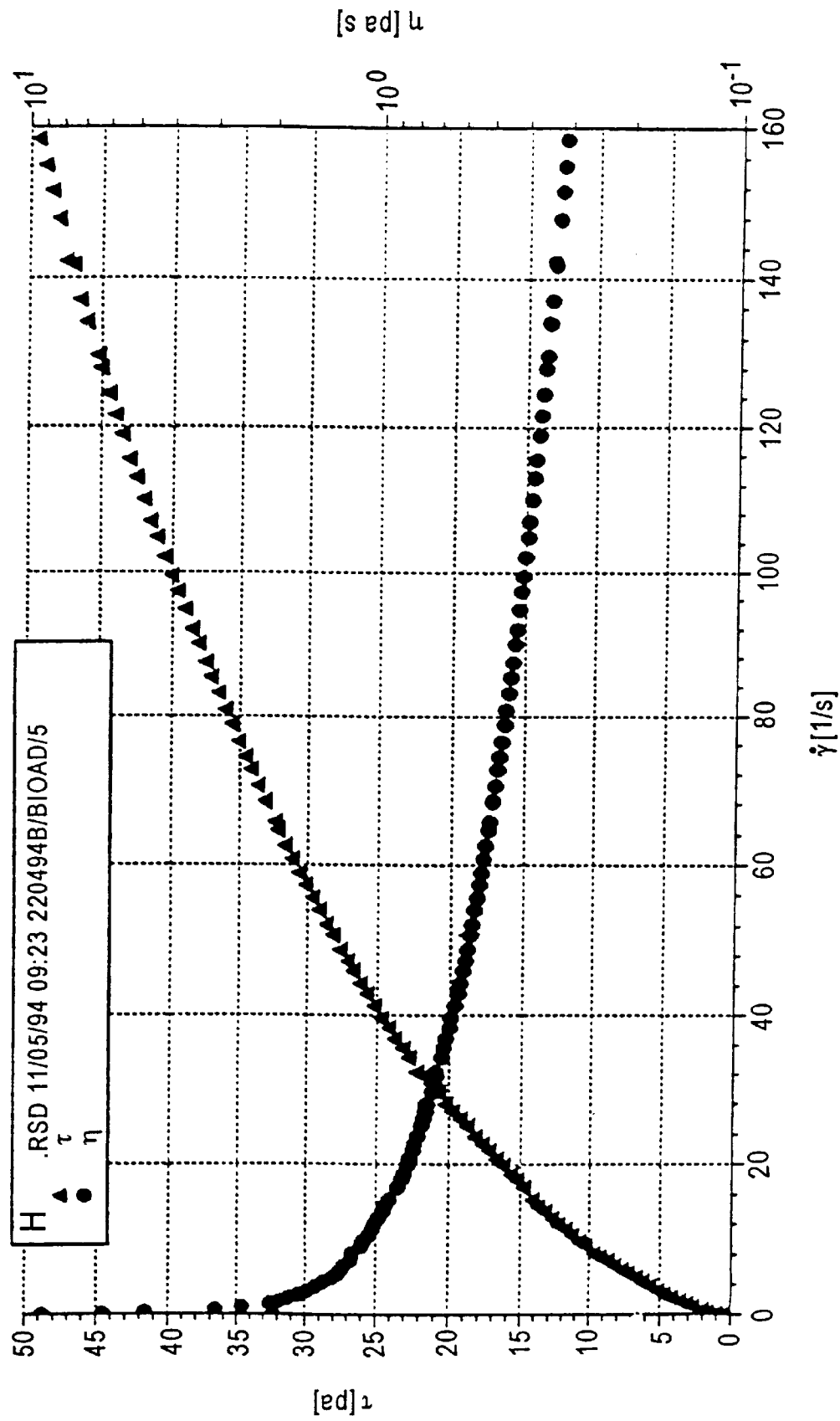

That is the intrinsic behaviour of Polycarbophil; instead, when it is mixed with other polymers, the gel is destructured: the creep limit value decreases until disappearing when passing from B (FIG. 1b) to D (FIG. 3b). Among the investigated compositions containing 0.2% Polycarbophil, sample H exhibits the highest viscosity. Furthermore, its viscoelastic behaviour is particularly interesting, since the elastic modulus increases more markedly than the viscous modulus, which indicates that sample H tends to change from stiff gel to viscous polymer. Said behaviour seems to be due to the presence of hyaluronic acid and to result from the average molecular weight and from the molecular weight distribution of the polymers in solution (FIG. 4b).

Sample I, which is characterized by the presence of low molecular weight dermatan sulfate, has lower viscosity than sample H, associated with the lower average molecular

TABLE 3

Viscosity $\eta$ of bioadhesive matrices

| Comp. Ref. | A | B | C | D | E | F | G | H | I |
|---|---|---|---|---|---|---|---|---|---|
| $\eta/50\ S^{-1}$ (Pa · s) | | 0.800 | | 0.400 | | | | 0.550 | 0.220 |
| $\eta/0.5\ S^{-1}$ (Pa · s) | 100 | | 100 | | — | — | 73 | | |

Viscosity $\eta$ was measured in Pascal.sec (Pa · s).

Oscillatory measurements

The samples (A,B,C,D,G,H, and I) were analyzed with a viscometer HAAKE® RS100, with flat-cone measurement system C35/4° at 23° C., with oscillation frequency varying from 0.0464 to 4.64 Hz and an applied stress of 0.50 Pa for samples B, D, H and I and of 4.00 Pa for samples A, C and G.

Figure 5A:
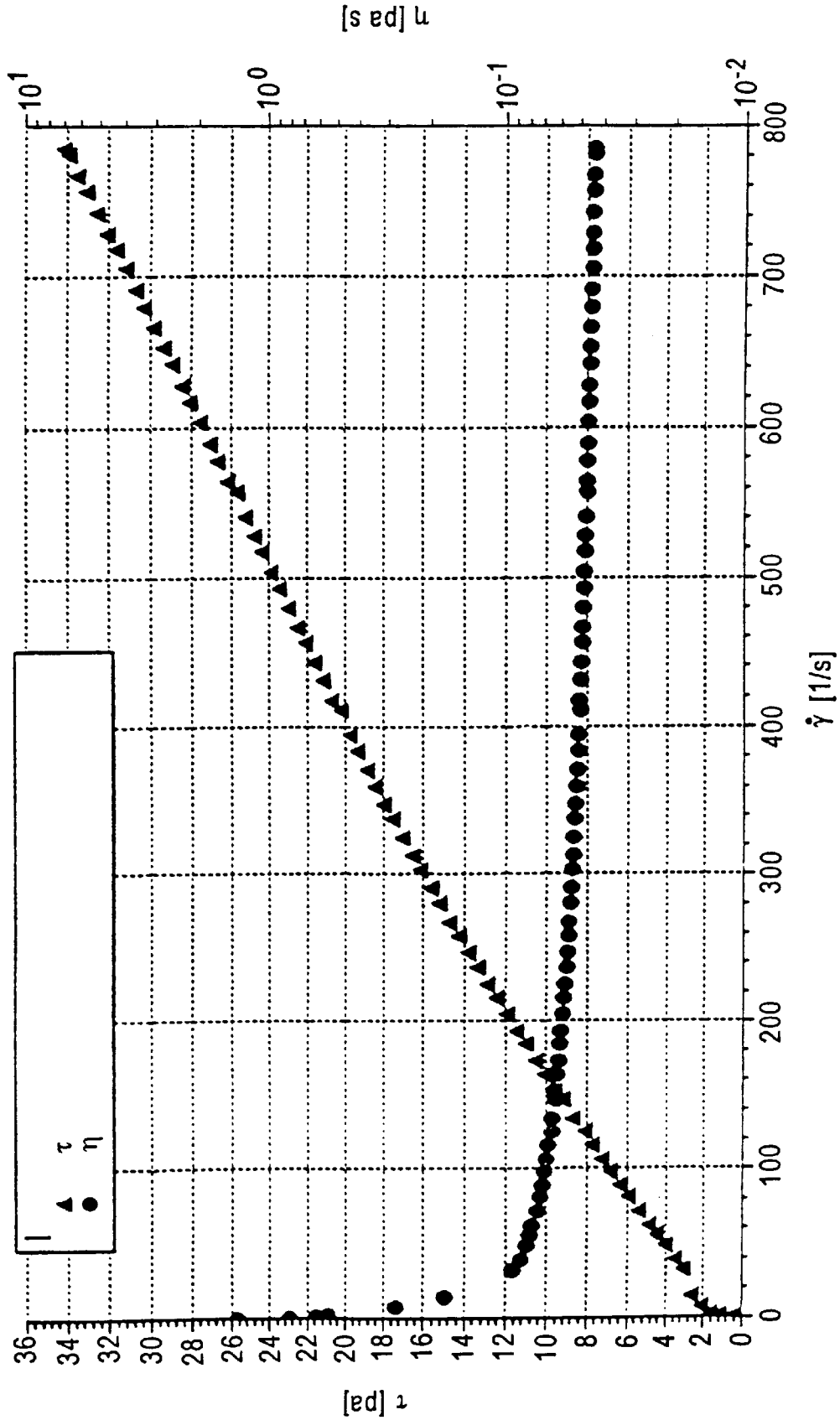

The oscillatory measurements, made to distinguish the "viscous" from the "elastic" character of the formulations, gave the results shown in FIG. 1b to 7b.

weight of the polysaccharide. In any case, said sample exhibits an interesting behaviour, analogous to that of newtonian liquids, the trend of the stress $\tau$/shear rate $\dot{\gamma}$ ratio being almost linear (FIGS. 5a, b).

Figure 6A:
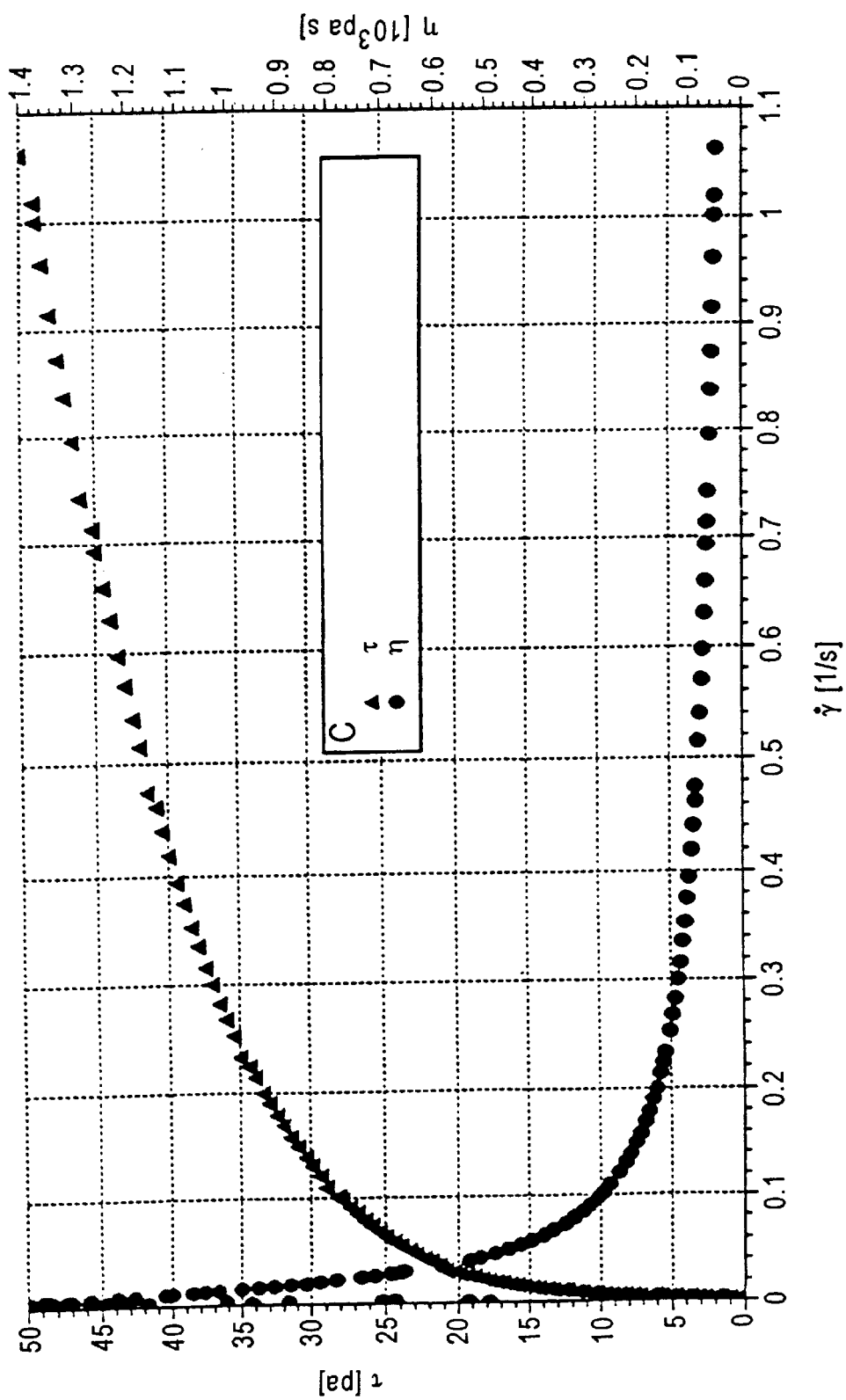
Figure 6B:
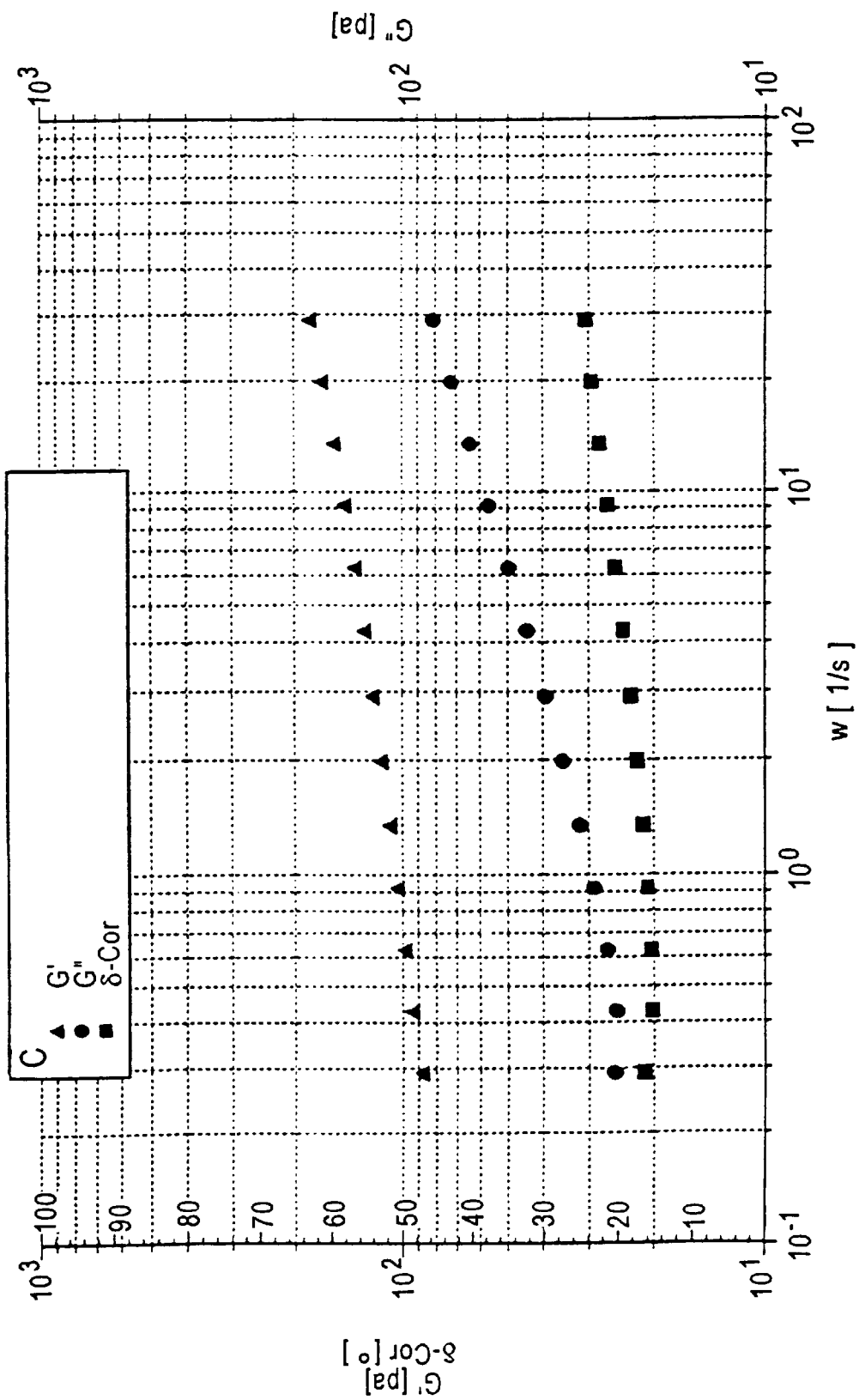

Sample C, compared with sample A, appears as a polymer solution rather than a stiff gel, which indicates that the physicochemical properties of the polysaccharide hyaluronic acid prevail over those of Polycarbophil (FIG. 6b).

Sample G is substantially a very viscous polymer solution. The curve representing the viscous modulus intersects the curve representing the elastic modulus at high angular speed values, which suggest the presence of a high average molecular weight polymer and a good molecular weight distribution (FIG. 7b).

It may be noted that the association of synthetic polymers, such as Polycarbophil and polyvinyl alcohol, with biopolymers, such as alginic acid, hyaluronic acid and dermatan sulfate, yields compositions with a marked bioadhesive behaviour and with the viscous character prevailing over the elastic one. This is an undoubted advantage, the "adhesiveness" being a property more closely related to the viscous modulus than to the elastic one and being the basis of the film-forming ability of said compositions.

In fact, if the "still gel" type rheological behaviour of Polycarbophil is modified by adding the aforesaid compositions with a viscous component, said compositions show not only improved adhesive properties but above all an improved film-forming ability. Thanks to their improved bioadhesiveness and viscosity, the compositions of the invention can provide stable film on the tissue to be treated, securing a better contact surface between the compositions and the same tissue and, consequently, a more adequate protection and/or moisturizing.

According to the aforesaid experimental results, the compositions of the invention have higher bioadhesive and, in particular, mucoadhesive properties than Polycarbophil, which is to date regarded as the molecule with the best bioadhesive properties, utilized in various formulations suitable for moisturizing mucous membranes and for releasing drugs at a controlled rate after oral or topical administration.

The bioadhesive compositions of the invention, formulated as hydrogels and/or viscous solutions with varying rheological consistency (from semisolid to apparently liquid) depending on the intended applications, are therefore meant to treat pathological conditions or even less severe alterations associated with the so-called paraphysiological situations in the following districts:

Cutaneous:

a) due to their moisturizing properties, useful in dryness/dehydration conditions caused by environmental factors or deriving from particular pharmacological treatments (e.g. keratolytic) or secondary to other diseases, e.g. eczema and dermatitis, or in situations for which tissue moisturizing is very important, e.g. decubitus ulcers:

b) due to their bioadhesive properties, in association with antimycotics, steroid and non-steroid anti-inflammatory agents or antibacterial agents for treating mycosis, burns and ulcers of different nature.

Ophthalmic:

a) as moisturizers/humectants in the treatment of disorders such as keratitis sicca or neuroparalytica, or of diseases simply caused by atmospheric factors or by foreign bodies fitting over the cornea, such as contact lenses;

b) as mucoadhesive matrix capable of increasing the contact time of specific drugs contained therein, necessary for the pathology under treatment.

The intraocular concentration of a drug is partly determined by the rate of its elimination from the conjunctival and episcleral circle. In fact, the typical vasodilatation of the eye involves a faster outflow of the active principle administered: it is, therefore, very important to prolong the contact time between the drug and the corneal epithelium. In particular, said drugs may be for example anti-inflammatory agents, anti-histamines for treating external eye diseases of allergic origin, antimycotics for treating keratites, specific antibiotics for treating viral infections, or antiglaucomatous or vasoactive agents.

Buccal:

a) in the form of mouthwash or gel, due to their moisturizing characteristics for treating xerostomia, both caused by irradiating treatments and associated with Sjögren's syndrome, senility or administration of drugs, such as tricyclic antidepressants;

b) in the form of a specific mouthwash, gel or paste, associated with oral cavity disinfectants for daily hygiene, for treating infections, or associated with antimycotics/antibiotics and anti-inflammatory agents for treating diseases such as for example candidiasis, muguet, stomatomucositis, paradontopathy, dental plaque and dismicrobism.

Tracheobronchial;

a) in the form of vaporization, due to their moisturizing and humectant characteristics, for treating dryness;

b) associated with antibiotics/antibacterial agents and/or anti-inflammatory agents for treating the inflammation of the upper respiratory tract.

Vaginal:

a) in the form of gynaecologic wash, due to their humectant characteristics, for treating vaginites of various nature, accompanied by mucosal dryness;

b) as a matrix capable of releasing drugs at a controlled rate, in particular in association with specific antimycotics, antibacterial or anti-inflammatory agents.

Gastroenteric and rectal:

a) due to their mucoadhesive and film-forming properties, for treating diarrhoea and consequent dehydration, and due to their ability to gel when coming into contact with water;

b) as a drug-delivery system, associated with drugs that would be insufficiently or variably absorbed by other administration routes or requiring a hepatic by-pass.

We report hereinbelow for illustrative but not limitative purposes the following examples of the pharmaceutical compositions according to the present invention, useful per se for the treatment of dryness conditions in the aforesaid districts.

EXAMPLE 10

Ophthalmic fluid gel (by wt. % composition)
| | |
|---|---|
| Polyvinyl alcohol | 1.50 |
| Polycarbophil | 0.20 |
| Hyaluronic acid | 0.15 |
| Thimerosal | 0.01 |
| Sodium chloride | 0.65 |
| Disodium hydrogen phosphate.12 $H_2O$ | 0.30 |
| Sodium dihydrogen phosphate.2 $H_2O$ | 0.03 |
| Demineralized water | q.s. to 100 |

EXAMPLE 11

Eyewash (by wt. % composition)
| | |
|---|---|
| Polyvinyl alcohol | 0.15 |
| Polycarbophil | 0.20 |
| Hyaluronic acid | 0.15 |
| Thimerosal | 0.01 |
| Sodium chloride | 0.65 |
| Disodium hydrogen phosphate.12 $H_2O$ | 0.30 |
| Sodium dihydrogen phosphate.2 $H_2O$ | 0.03 |
| Demineralized water | q.s. to 100 |

EXAMPLE 12

Eyewash (by wt. % composition)
| | |
|---|---|
| Polycarbophil | 0.20 |
| Dermatan sulfate | 0.30 |
| Thimerosal | 0.01 |
| Sodium chloride | 0.65 |
| Disodium hydrogen phosphate.12 $H_2O$ | 0.30 |

| | |
|---|---|
| Sodium dihydrogen phosphate.2 H$_2$O | 0.03 |
| Demineralized water | q.s. to 100 |

EXAMPLE 13

Gynaecologic gel (by wt. % composition)

| | |
|---|---|
| Polyvinyl alcohol | 1.50 |
| Triethanolamine | 1.50 |
| Polycarbophil | 1.00 |
| Sodium alginate | 1.00 |
| Methyl p-hydroxybenzoate | 0.10 |
| 2-Phenylethanol | 0.10 |
| Ethyl p-hydroxybenzoate | 0.10 |
| Demineralized water | q.s. to 100 |

EXAMPLE 14

Dermatologic gel (by wt. % composition)

| | |
|---|---|
| Polyvinyl alcohol | 1.50 |
| Triethanolamine | 1.50 |
| Polycarbophil | 1.00 |
| Sodium alginate | 2.00 |
| Methyl p-hydroxybenzoate | 0.10 |
| 2-Phenylethanol | 0.10 |
| Ethyl p-hydroxybenzoate | 0.10 |
| Demineralized water | q.s. to 100 |

EXAMPLE 15

Dental gel (by wt. % composition)

| | |
|---|---|
| Polyvinyl alcohol | 1.50 |
| Triethanolamine | 1.50 |
| Polycarbophil | 1.00 |
| Sodium alginate | 3.00 |
| Methyl p-hydroxybenzoate | 0.10 |
| 2-Phenylethanol | 0.10 |
| Ethyl p-hydroxybenzoate | 0.10 |
| Demineralized water | q.s. to 100 |

The compositions of the present invention may also be used as vehicles of active principles useful for the treatment of cutis and mucous membranes diseases. We report hereinbelow for illustrative but not limitative purposes the following examples.

EXAMPLE 16

Gynaecologic gel (by wt. % composition)

| | |
|---|---|
| 2-Phenylphenol | 0.30 |
| Methyl p-hydroxybenzoate | 0.10 |
| Ethyl p-hydroxybenzoate | 0.10 |
| *Eumulgin HRE 40 ® | 1.00 |
| Triethanolamine | 0.20 |
| Polycarbophil | 1.00 |
| Polyvinyl alcohol | 1.50 |
| Hyaluronic acid | 0.10 |
| Vitamin A Palmitate 2,000 IU/g | 0.20 |
| Hyaluronic acid salt (Ex. 7) | 0.06 |
| Chondroitin 6-sulfate | 0.20 |
| Demineralized water | q.s. to 100 |

*Eumulgin HRE 40 ® : polyoxyethylenated caster oil

EXAMPLE 17

Dermatologic gel (by wt. % composition)

| | |
|---|---|
| 2-Phenylphenol | 0.30 |
| Methyl p-hydroxybenzoate | 0.10 |
| Ethyl p-hydroxybenzoate | 0.10 |
| Eumulgin HRE 40 ® | 1.00 |
| Triethanolamine | 0.275 |
| Polycarbophil | 1.00 |
| Polyvinyl alcohol | 1.00 |
| Hyaluronic acid | 0.15 |
| Vitamin A Palmitate 2,000 IU/g | 0.20 |
| Hyaluronic acid salt (Ex. 6) | 0.06 |
| Dodecenedioic acid | 0.05 |
| Demineralized water | q.s. to 100 |

EXAMPLE 18

Gynaecologic solution (by wt. % composition)

| | |
|---|---|
| 2-Phenylphenol | 0.30 |
| Methyl p-hydroxybenzoate | 0.10 |
| Ethyl p-hydroxybenzoate | 0.10 |
| Eumulgin HRE 40 ® | 1.00 |
| Hydroxyethylcellulose | 0.50 |
| Lactic acid (80%) | 2.00 |
| Triethanolamine | 2.30 |
| Polycarbophil | 0.20 |
| Polyvinyl alcohol | 0.30 |
| Hyaluronic acid | 0.15 |
| Vitamin A Palmitate 2,000 IU/g | 0.20 |
| Hyaluronic acid salt (Ex. 3) | 0.20 |
| Demineralized water | q.s. to 100 |

EXAMPLE 19

Dermatologic gel (by wt. % composition)

| | |
|---|---|
| 2-Phenylphenol | 0.30 |
| Methyl p-hydroxybenzoate | 0.10 |
| Ethyl p-hydroxybenzoate | 0.10 |
| Eumulgin HRE 40 ® | 1.00 |
| Polycarbophil | 1.00 |
| Polyvinyl alcohol | 1.50 |
| Dermatan sulfate | 0.15 |
| Vitamin A Palmitate 2,000 IU/g | 0.20 |
| Quercetin | 0.01 |
| Dermatan sulfate salt (Ex. 4) | 0.06 |
| Triethanolamine | 0.25 |
| Chondriotin 6-sulfate | 0.20 |
| Demineralized water | q.s. to 100 |

EXAMPLE 20

Gynaecologic gel (by wt. % composition)

| | |
|---|---|
| Glycerin | 10.00 |
| Eumulgin HRE 40 ® | 2.00 |
| Polycarbophil | 1.00 |
| Hyaluronic acid | 0.30 |
| Triethanolamine | 0.25 |
| Vitamin A Palmitate 2,000 IU/g | 0.20 |
| Methyl p-hydroxybenzoate | 0.10 |
| Ethyl p-hydroxybenzoate | 0.10 |
| 2-Phenylethanol | 0.15 |
| Methyl Paraben | 0.10 |
| Dodecenedioic acid, cetrimide salt | 0.05 |
| N-(2-hydroxyethyl)-hexadecanamide | 0.01 |
| Demineralized water | q.s. to 100 |

EXAMPLE 21

Eyewash (by wt. % composition)

| | |
|---|---|
| Polycarbophil | 0.20 |
| Dermatan sulfate salt (Ex. 5) | 0.30 |
| Thimerosal | 0.01 |
| Sodium chloride | 0.65 |
| Disodium hydrogen phosphate.12 H$_2$O | 0.30 |
| Sodium hydrogen phosphate.2 H$_2$O | 0.03 |
| Demineralized water | q.s. to 100 |

EXAMPLE 22

Dental gel (by wt. % composition)

| | |
|---|---|
| Polyvinyl alcohol | 1.50 |
| Triethanolamine | 1.50 |
| Polycarbophil | 1.00 |
| Dermatan sulfate salt (Ex. 8) | 3.00 |
| Methyl p-hydroxybenzoate | 0.10 |
| 2-Phenylethanol | 0.10 |
| Ethyl p-hydroxybenzoate | 0.10 |
| Demineralized water | q.s. to 100 |

EXAMPLE 23

Dermatologic gel (by wt. % composition)

| | |
|---|---|
| Polyvinyl alcohol | 1.50 |
| Triethanolamine | 1.50 |
| Polycarbophil | 1.00 |
| Dermatan sulfate (Ex. 2) | 2.00 |
| Methyl p-hydroxybenzoate | 0.10 |
| 2-Phenylethanol | 0.10 |
| Ethyl p-hydroxybenzoate | 0.10 |
| Demineralized water | q.s. to 100 |

EXAMPLE 24

Gynaecologic gel (by wt. % composition)

-continued

| | |
|---|---|
| Polyvinyl alcohol | 0.20 |
| Polycarbophil | 1.00 |
| Hyaluronic acid | 0.10 |
| N,N'-bis-(2-hydroxyethyl)-nonandiamide | 0.20 |
| Glycerin | 10.00 |
| Propylene glycol | 1.00 |
| Hydrogenated castor oil (40)OE* | 1.00 |
| Tocopheryl acetate | 0.50 |
| Phenylethyl alcohol | 0.15 |
| Methyl p-hydroxybenzoate | 0.10 |
| Quercitin | 0.01 |
| Sodium hydroxide (30% by wt. solution) | 0.20 |
| Demineralized water | q.s. to 100 |

*Hydrogenated castor oil (40)OE is polyoxyethylenated with 40 moles ethylene oxide/mole.

EXAMPLE 25

Dental gel (by wt. % composition)

| | |
|---|---|
| Polyvinyl alcohol | 1.50 |
| Polycarbophil | 1.00 |
| Sodium alginate | 3.00 |
| N,N'-bis-(2-hydroxyethyl)-nonandiamide | 0.20 |
| Triethanolamine | 1.50 |
| Methyl p-hydroxybenzoate | 0.10 |
| 2-Phenylethanol | 0.10 |
| Ethyl p-hydroxybenzoate | 0.10 |
| Demineralized water | q.s. to 100 |

EXAMPLE 26

Dental gel (by wt. % composition)

| | |
|---|---|
| Polyvinyl alcohol | 0.200 |
| Polycarbophil | 0.200 |
| Hyaluronic acid | 0.050 |
| N,N'-bis-(2-hydroxyethyl)-nonandiamide | 1.000 |
| Trans-2-dodecendioic acid | 0.005 |
| Xylitol | 7.500 |
| Carboxymethylcellulose sodium salt | 4.500 |
| Hydrogenated castor oil (40)OE* | 0.500 |
| 2,4-Dichlorobenzylic alcohol | 0.150 |
| Cytromint | 0.150 |
| Colour CI 42090 | 0.025 |
| Colour CI 19140 | 0.015 |
| Demineralized water | q.s. to 100 |

*Hydrogenated castor oil (40)OE is polyoxyethylenated with 40 moles ethylene oxide/mole.

EXAMPLE 27

Dental mouthwash (by wt. % composition)

| | |
|---|---|
| Polycarbophil | 0.100 |
| Hyaluronic acid | 0.0500 |
| PTC* | 57.1429 |
| N,N'-bis-(2-hydroxyethyl)-nonandiamide | 0.0100 |
| Trans-2-dodecendioic acid | 0.005 |
| Xylitol | 7.5000 |
| Polysorbate 20 | 1.0000 |
| 2,4-Dichlorobenzylic alcohol | 0.1500 |
| Cytromint | 0.1000 |
| Colour CI 42090 | 0.1000 |
| Demineralized water | q.s. to 100 |

*PTC (Polyphenolic Tea Complex) indicates an aqueous extract containing 0.15–0.4% by weight of D(*)-catechin, obtained by treating 1 kg of green tea (leaves) in demineralized water (20–30 l), at a temperature of 60–80° C., for a period of 10–30 minutes.

EXAMPLE 28

Dental spray (by wt. % composition)

| | |
|---|---|
| Polyvinyl alcohol | 0.200 |
| Hyaluronic acid | 0.050 |
| N,N'-bis-(2-hydroxyethyl)-nonandiamide | 1.000 |
| Trans-2-dodecendioic acid | 0.005 |
| Xylitol | 7.500 |
| Hydrogenated castor oil (40)OE* | 0.500 |
| Cytrimint | 0.180 |
| 2,4-Dicholorobenzylic alcohol | 0.150 |
| Demineralized water | q.s. to 100 |

*Hydrogenated castor oil (40)OE is polyoxyethylenated with 40 moles ethylene oxide/mole.

We claim:

1. A highly bioadhesive and mucoadhesive aqueous composition useful in the rehydration of the skin and mucosal tissues and/or as a vehicle for active principles in percutaneous absorption, comprising:
   (a) polycarbophil in an amount ranging from about 0.1 to 2% by wt;
   (b) polyvinyl alcohol in an amount ranging from about 0.1 to 4% by weight; and
   (c) a biopolymer selected from the group consisting of:
      (1) hyaluronic acid and salts thereof, in an amount ranging from about 0.05% to 5% by weight, said hyaluronic acid having an average molecular weight ranging from about 800,000 to 1,200,000 daltons,
      (2) dermatan sulfate and salts thereof, in an amount ranging from about 0.05% to 5% by weight, said dermatan sulfate having an average molecular weight of about 5,000 to 8,000 daltons;
      (3) chondroitin sulfate, and salts thereof; and
      (4) alginic acid and salts thereof in an amount ranging from about 0.5% to 5% by weight.

2. The aqueous composition according to claim 1, characterized in that said hyaluronic acid salts are selected from the group consisting of zinc salt, mixed salt with biotin and ethylenediamine, and mixed salt with traumatic acid and ethylenediamine.

3. The aqueous composition according to claim 1, characterized in that said dermatan sulfate salts are selected from the group consisting of lithium, zinc and tetrabutylammonium salts, mixed salt with biotin and ethylenediamine, and mixed salt with traumatic acid and ethylenediamine.

4. The aqueous composition according to claim 1, characterized in that said active to be vehiculated in percutaneous absorption is selected from the group consisting of antimycotics, steroid and non-steroid anti-inflammatory agents, antibacterial agents, anti-histamines, antibiotics, antiglaucomatous agents, vasoactive agents and disinfectants.

5. A process for the preparation of a bioadhesive and mucoadhesive aqueous composition of claim 1 comprising the following steps:
   (a) complete homogenization of said polycarbophil and polyvinyl alcohol in water, wherein homogenization is carried out in a single pot, or in two separate pots with subsequent combination of the resulting masses under continuous stirring;
   (b) preparation of a homogeneous solution of one of said biopolymers in water; and
   (c) adding of the solution obtained in (b) to the mixture obtained in (a), under continuous stirring, until complete homogenization of a mass is obtained.

6. The process according to claim 5, where a water solution of a thickening agent is added under stirring to the mass obtained in step (c).

7. The process according to claim 6, characterized in that said thickening agent is triethanolamine.

8. A method for treating skin and mucosa tissues to dryness and dehydration, which comprises administration of a bioadhesive and mucoadhesive aqueous composition as defined in claim 1.

9. The aqueous composition according to claim 1, characterized in that said mucosal tissues are selected from the group consisting of cutaneous, ophthalmic, buccal, tracheobronchial, vaginal, gastroenteric and rectal tissues.

10. A vehicle comprising active principles for percutaneous absorption in a bioadhesive and mucoadhesive aqueous composition as defined in claim 1.

11. A dermatan sulfate salt selected from the group consisting of mixed salt with biotin and ethylenediamine, and mixed salt with traumatic acid and ethylenediamine.

12. The salt according to claim 11, characterized in that said dermatan sulfate has an average molecular weight ranging from 5,000 to 8,000 daltons.

13. A hyaluronic acid salt selected from the group consisting of mixed salt with biotin and ethylenediamine and mixed salt with traumatic acid and ethylenediamine.

14. The salt according to claim 13, characterized in that said hyaluronic acid has an average molecular weight ranging from about 800,000 to 1,200,000 daltons.

15. The aqueous composition according to claim 1, wherein said polycarbophil is a polyacrylic acid cross-linked with divinylglycol.

* * * * *